US006248583B1

(12) United States Patent
Aron et al.

(10) Patent No.: US 6,248,583 B1
(45) Date of Patent: Jun. 19, 2001

(54) CHROMOSOMALLY-ENCODED MEMBRANE PROTEIN OF BORRELIA BURGDORFERI

(75) Inventors: Lieselotte Aron; Felipe Cabello, both of Hartsdale; Henry P. Godfrey, Scarsdale; Ira Schwartz, Spring Valley, all of NY (US)

(73) Assignee: New York Medical College, Valhalla, NY (US)

( * ) Notice: Subject to any disclaimer, the term of this patent is extended or adjusted under 35 U.S.C. 154(b) by 0 days.

(21) Appl. No.: 08/313,412

(22) Filed: Sep. 27, 1994

(51) Int. Cl.[7] .............................. C12N 15/00; C12N 5/00; C07H 21/02; C07H 21/04
(52) U.S. Cl. ................... 435/325; 435/320.1; 435/252.3; 536/23.1; 536/23.7
(58) Field of Search .......................... 530/350; 536/23.5, 536/24.32, 23.1, 27.7; 435/320.1, 325, 252.3

(56) References Cited

U.S. PATENT DOCUMENTS 5,643,751    7/1997    Robinson et al. .

OTHER PUBLICATIONS

Boehringer Mannheim Biochemicals 1991 Catalog, p. 557, 1991.*
Lazar et al. Mol. Cell Biol. 8(3): 1247–52, Mar. 1988.*
Burgess et al. J. Cell Biol. 111:2129–38, Nov. 1990.*
J.A. Parsons et al. (Ed) "Peptide Hormones", published by University Park Press (Baltimore); see Chapter 1, Rudinger, pp. 1–6, Jun. 1976.*
Fuchs et al. Mol. Microbiol. 6(4); 503–509 (see abstract), 1992.*
Barbour et al. Annals of the New York Academy of Sciences 539:144–153, Aug. 1988.*
S. Bergstrom, et al., "Molecular Analysis of Linear Plasmid–Encoded Major Surface Proteins, OspA and OspB, of the Lyme Disease Spirochaete *Borrelia burgdorferi,*" *Molecular Microbiol.,* 3(4):479–86 (1989).
Simpson, W.J., et al., "Nucleotide Sequence and Analysis of the Gene in *Borrelia burgdorferi* Encoding the Immunogenic P39 Antigen," *FEMS Microbiol. Letters* 119:381–88 (1994).
Barbour, A.G., "Annals of Internal Medicine: The Diagnosis of Lyme Disease: Rewards and Perils," *Annals of Internal Medicine,* 110(7):501–502 (1989).
Corpuz, M., et al., "Problems in the Use of Serologic Tests for the Diagnosis of Lyme Disease," *Intern Med* 151:1837–40 (1991).
Rahn, D.W., et al., "Conferences and Reviews: Lyme Disease," Department of Internal Medicine, Section of Rheumatology, Yale University School of Medicine, New Have, Connecticit.

Barbour, A.G., "Issues of the Day Biological and Social Determinants of the Lyme Disease Problem," *Infectious Agents and Disease,* 1:50–61 (1992).
Fuchs, R., et al., "Molecular Analysis and Expression of a *Borrelia burgdorferi* Gene Encoding a 22kDa Protein (pC) in *Escherichia coli,*" 6(4):503–509 (1992).
Marconi, R.T., et al., "Variability of osp Genes and Gene Products among Species of Lyme Disease Spirochetes," *Infection and Immunity,* 61(6):2611–17 (1993).
Lam, T.T., et al., "Outer Surface Proteins E and F of *Borrelia burgdorferi,* the Agent of Lyme Disease," *Infection and Immunity,* 62(1):290–98 (1994).
Fikrig, E., et al., "Protection of Mice Against the Lyme Disease Agent by Immunizing with Recombinant OspA," *Reports,* pp. 553–555 (Oct. 1990).
Fikrig, E., et al., "Evasion of protective immunity by *Borrelia burgdorferi* by Truncation of Outer Surface Protein B," *Proc. Natl. Acad. Sci. USA,* 90:4092–96 (1993).
Rasiah, C., et al., Purification and Characterization of a Tryptic Peptide of *Borrelia burgorferi* Flagellin, which Reduces Cross–reactivity in Immunoblots and ELISA, *Journal of General Microbiology,* 138:147–154 (1992).
Hyde, F.W., et al., "Detection of Antigens in Urine of Mice and Humans Infected with *Borrelia burgdorferi,* Etiologic Agent of Lyme Disease," *Journal of Clin. Microbiol.,* 27(1):58–61 (1989).
Scriba, Marianne, et al., "The 39–Kilodalto Protein of *Borrelia burgdorferi*: a Target for Bacterial Human Monoclonal Antibodies," *Infection and Immunity,* 61(10):4523–26 (1993).
Comstock, L.E., et al., "A Monoclonal Antibody to OspA Inhibits Association of *Borrelia burgdorferi* with Human Endothelial Cells," *Infection and Immunity,* 61(2):423–31 (1993).
Simpson et al., "Nucleotide Sequence and Analysis of the Gene in *Borrelia brugdorferi* incoding the Immunoginic p. 39 Antigen," *FEMS Microbiology Letters,* vol. 119, 1994, pp. 381–388.*

* cited by examiner

Primary Examiner—Marianne P. Allen
(74) Attorney, Agent, or Firm—Nixon Peabody LLP (57) ABSTRACT

The present invention relates to an isolated membrane protein or polypeptide encoded by chromosomal DNA of *Borrelia burgdorferi* (e.g., BmpC). This protein is encoded by a DNA molecule (e.g., bmpC) and is useful in vaccines to prevent infection by *Borrelia burgdorferi,* while antibodies raised against this protein can be employed in passively immunizing those already infected by the organism. Both these proteins and antibodies may be utilized in diagnostic assays to detect *Borrelia burgdorferi* and immune response in tissue or body fluids. Likewise, the DNA molecule can be used for detection of this organism.

8 Claims, 4 Drawing Sheets

```
         20             40             60             80            100            120
          •              •              •              •              •              •
AAAAATTGATTTTTCCTACTACTGTGTTTTTATTAATGCTAGAAGTATTTTTTAAAAGGGATTATTAAAATTTTATTTTATAAATAAAGAATACTGCTTGTTAGTAAAATAAAGTTAAT 140            160            180            200            220
          •              •              •              •              •
ATTTTAATTTTTAAAAAATTTAGAATTTTAAAAAAAAATATAAGGAGAGGATTAATT TTG TTT AAA AGA TTT ATT TTT ATT ACT TTA TCT TTA TTA GTA TTT
                                                          Met Phe Lys Arg Phe Ile Phe Ile Thr Leu Ser Leu Leu Val Phe 240            260            280            300
          •              •              •              •
GCT TGT TTT AAA TCT AAT AAA AAG TCT ATT AAA TCT GAC AAA GTT GTT GTA GGT GTT TTG GCT CAT GGT AGC TTT TAT GAT AAA GGC TAT
Ala Cys Phe Lys Ser Asn Lys Lys Ser Ile Lys Ser Asp Lys Val Val Val Gly Val Leu Ala His Gly Ser Phe Tyr Asp Lys Gly Tyr 320            340            360            380            400
          •              •              •              •              •
AAT CAA AGC GTT CAT GAT GGT GTT GTA AAA CTT AGG GAT AAT TTT GGA ATA AAG CTT ATA ACT AAA TCT TTA AGA CCT TAT CCT ATT GAG
Asn Gln Ser Val His Asp Gly Val Val Lys Leu Arg Asp Asn Phe Gly Ile Lys Leu Ile Thr Lys Ser Leu Arg Pro Tyr Pro Ile Glu 420            440            460            480
          •              •              •              •
GGT AAA AGA CTT CTT ACT GTT GAT GAG GCA ATG ACT GAG GAT GCT TAT GAG GTT CAA AAA AAT CCT TTA AAT CTT TTT TGG TTG ATT GGA
Gly Lys Arg Leu Leu Thr Val Asp Glu Ala Met Thr Glu Asp Ala Tyr Glu Val Gln Lys Asn Pro Leu Asn Leu Phe Trp Leu Ile Gly 500            520            540            560            580
          •              •              •              •              •
TAC CGA TTT TCT GAC TTG TCA GTT AAG CTT TCC TAT GAA CGT CCA GAT ATT TAT TAT GGT ATT ATA GAT GCT TTT GAT TAT GGT GAT ATT
Tyr Arg Phe Ser Asp Leu Ser Val Lys Leu Ser Tyr Glu Arg Pro Asp Ile Tyr Tyr Gly Ile Ile Asp Ala Phe Asp Tyr Gly Asp Ile 600            620            640            660
          •              •              •              •
CAA GTT CCT AAG AAT TCC TTG GCT ATT AAG TTT AGA AAT GAA GAG GCT GCA TTT TTA GCT GGG TAT ATT GCT GCT AAG ATG AGC AGA AAA
Gln Val Pro Lys Asn Ser Leu Ala Ile Lys Phe Arg Asn Glu Glu Ala Ala Phe Leu Ala Gly Tyr Ile Ala Ala Lys Met Ser Arg Lys 680            700            720            740            760
          •              •              •              •              •
GAA AAG ATT GGA TTT TTA ACA GGT CCT ATG AGT GAG CAT TTA AAA GAT TTT AAG TTT GGT TTT AAG GCT GGA ATT TTT TAT GCC AAT CCT
Glu Lys Ile Gly Phe Leu Thr Gly Pro Met Ser Glu His Leu Lys Asp Phe Lys Phe Gly Phe Lys Ala Gly Ile Phe Tyr Ala Asn Pro 780            800            820            840
          •              •              •              •
AAA TTA AGA TTA GTT TCA AAA AAA GCA CCT TCT CTT TTT GAT AAG GAG AAA GGC AAA GCA ATG GCT CTA TTC ATG TAT AAA GAA GAT AAA
Lys Leu Arg Leu Val Ser Lys Lys Ala Pro Ser Leu Phe Asp Lys Glu Lys Gly Lys Ala Met Ala Leu Phe Met Tyr Lys Glu Asp Lys 860            880            900            920            940
          •              •              •              •              •
GTA GGC GTT ATT TTT CCA ATA GCT GGT ATA ACT GGT CTT GGA GTT TAT GAC GCT GCT AAG GAG CTT GGA CCT AAA TAT TAT GTT ATT GGT
Val Gly Val Ile Phe Pro Ile Ala Gly Ile Thr Gly Leu Gly Val Tyr Asp Ala Ala Lys Glu Leu Gly Pro Lys Tyr Tyr Val Ile Gly 960            980           1000           1020
          •              •              •              •
TTA AAT CAA GAT CAA TCA TAT ATT GCA CCT CAA AAT GTT ATT ACT TCA ATA ATT AAG GAT ATT GGT AAG GTT ATT TAT TCT ATT TCA TCA
Leu Asn Gln Asp Gln Ser Tyr Ile Ala Pro Gln Asn Val Ile Thr Ser Ile Ile Lys Asp Ile Gly Lys Val Ile Tyr Ser Ile Ser Ser 1040           1060           1080           1100           1120
          •              •              •              •              •
GAG TAT ATT AAT AAT AGA GTT TTT AAG GGT GGA ATT ATT ATT GAT CGG GGG TTA AAG GAA GGA GTA ATA GAA ATT GTT AAG GAT CCC GAT
Glu Tyr Ile Asn Asn Arg Val Phe Lys Gly Gly Ile Ile Ile Asp Arg Gly Leu Lys Glu Gly Val Ile Glu Ile Val Lys Asp Pro Asp 1140           1160           1180           1200
          •              •              •              •
GTT TTA AAC AAT AGG TTG GTT GAT GAA GTT ATT GAT CTA GAA AAT AAA ATA ATA AGT GGA GAA ATT ATT GTT CCT GAT AGT GAA TAT GCA
Val Leu Asn Asn Arg Leu Val Asp Glu Val Ile Asp Leu Glu Asn Lys Ile Ile Ser Gly Glu Ile Ile Val Pro Asp Ser Glu Tyr Ala 1220           1240           1260           1280
          •              •              •              •
TTT GAT TTA TTT AAA TCA AAG TTA TAAACTACTTAAATATAGCTTTGTTTGTAAAGGGGAAATAGTTTATGAATAAAATAT
Phe Asp Leu Phe Lys Ser Lys Leu
```

FIG. 1

```
BmpC    MFKRFIFITL-SLLVFACFKSNKKSIKSDKVVVGVLAHGSFYDKGYNQSVHDGVV     54
BmpA    MNKILLLILLESIVFLSCSGKGSLGSEIPKV--SLIIDGTFDDKSFNESALNGVK     53
BmpB    M-RIVIFIF--GILLTSCFSRNGIESSSKKIKISMLVDGVLDDKSFNSSANEALL     52
        *  . ..*   ...  .*  .. . . *.  ... .* . **..* *. ...

BmpC    KLRDNFGIKLITKSLRPYPIEGKRLLTVDEAMTEDAYEVQKNPLNLFWLIGYRFS    109
BmpA    KVKEEF--KI--ELVLKESSS--------NSYLSDLEGLKDAGSDLIWLIGYRFS     96
BmpB    RLKKDFPEDI--EEVFSCAISG-----VYSSYVSDLDNLKRNGSDLIWLVGYMLT    100
        .....*    ..  . .  ..         .. .*  ... . .*.**.**...

BmpC    DLSVKLSYERPDIYYGIIDAFDYGDIQVPKNSLAIKFRNEEAAFLAGYIAAKMSR    164
BmpA    DVAKVAALQNPDMKYAIIDPIYSND-PIPANLVGMTFRAQEGAFLTGYIAAKLSK    150
BmpB    DASLLVSSENPKISYGIIDPFYGADVQIPENLIAVVFRVEQGAFLAGYIAAKKSF    155
        *  .   . ..*.. *.***..  .* ..* * ... ** ...***.****** *

BmpC    KEKIGFLTGPMSEHLKDFKFGFKAGIFYANPKLRLVSKKAPSLFDKEKGKAMALF    219
BmpA    TGKIGFLGGIEGEIVDAFRYGYEAGAKYANKDIKISTQYIGSFADLEAGRSVATR    205
BmpB    SGKIGFIGGMKGNIVDAFRYGYESGAKYANKDIEIISEYSNSFSDVDIGRTIASK    210
        ..****..*   .. ...*..*...*  ***  .....  .. *. * . *...*

BmpC    MYKEDKVGVIFPIAGITGLGVYDAAKELGPKYYVIGLNQDQSYIAPQNVITSIIK    274
BmpA    MYSDE-IDIIHHAAGLGGIGAIEVAKELGSGHYIIGVDEDQAYLAPDNVITSTTK    259
BmpB    MYSLG-IDVIHFAAGLAGIGVIEAAKNLGDGYYVIGADQDQSYLAPKNFITSVIK    264
        **. .  ...*   **..*.*. ..**.**  .*.** ..**.*.**.* ***..*

BmpC    DIGKVIYSISSEYI-NNRVFKGGIIIDRGLKEGVIEIVKDPDVLNNRLVDEVIDL    328
BmpA    DVGRALNIFTSNH-LKTNTFEGGKLINYGLKEGVVGFVRNPKMISFELEKEIDNL    313
BmpB    NIGDALYLITGEYILNNNVWEGGKVVQMGLRDGVIGL---PNANEFEY---IKVL    313
        ..* ..  .....   ......** ... **..**...   *.  .     . *

BmpC    ENKIISGEIIVPDSEYAFDLFKS---KL    353
BmpA    SSKIINKEIIVPSNKESYEKFLKEFI--    339
BmpB    ERKIVNKEIIVPCNQEEYENFIKQILKL    341
        ..**.. *****  .. ... * .
```

*FIG. 2A*

```
BmpC    MFKRFI--FITL--SLLVFACFKSNKK------SIKSDKVVVGVLAH-GSFYDKG   -44
        :       :     :  :::              :::      :    ::
TmpC    MREKWVRAFAAVFCAMLLIGCSKSDRPQMGNAGGAEGGDFVVGMVTDSGDIDDKS   -55

BmpC    YNQSVHDGVVKLRDNFGIKLITKSLRPYPIEGKRLLTVDEAMTEDAYEVQKNPLN   -99
        ::  :   :           :           :                 :    :
TmpC    FNQQVWEGISRFAQENNAK------CKYVTAST---DAEYVPSLSAFADENMGLV  -101

BmpC    LFWLIGYRFSDLSVKLSYERPDIYYGIIDAFDYGDIQVPKNSLAIKFRNEEAAFL  -154
           :            : :    :::       :  :    :  :    :  ::
TmpC    V--ACGSFLVEAVIETSARFPKQKFLVIDAV----VQDRDNVVSAVFGQNEGSFL  -150

BmpC    AGYIAA---KMSRKEKIGFLTGPMSEHLKDFKFGFKAGIFYANPKLRLVSKKAPS  -206
         :  ::    :    :    ::   :     :   :  :: ::     :    :   :
TmpC    VGVAAALKRKEAGKSAVGFIVGMELGMMPLFEAGFEAGVKAVDPDIQVVVEVANT  -205

BmpC    LFDKEKGKAMALFMYKEDKVGVIFPIAGITGLGVYDAAKE---LGPKYYVIGLNQ  -258
         :  :: :  :    :      :    : ::::  ::  ::    :       :::
TmpC    FSDPQKGQALAAKLY-DSGVNVIFQVAGGTGNGVIKEARDRRLNGQDVWVIGVDR  -259

BmpC    DQ----SYIAPQNVITSIIKDIGKVIYSISSEYINNRVFKGGIIIDRGLKEGVIE  -309
        ::    :     :           :          :         :  ::   :  ::
TmpC    DQYMDGVYDGSKSVVLTSMVKRADVAAERISKMAYDGSFPGGQSIMFGLEDKAVG  -314

BmpC    IVKDPDVLNNRLVDEVIDLENKIISGEIIVPDSEYAFDLFKSKL            -353
         :        :             :  ::  :   ::  ::
TmpC    IPEENPNLSSAVMEKIRSFEEKIVSKEIVVPVRSA-----RMMN            -353
```

CHROMOSOMALLY-ENCODED MEMBRANE PROTEIN OF BORRELIA BURGDORFERI

This work was supported by Grant No. C-001102 from the New York State Tick-borne Disease Institute and by NIH Grant Nos. AR41511 and CA34141.

FIELD OF THE INVENTION

The present invention relates to a chromosomally-encoded membrane protein or polypeptide of *Borrelia burgdorferi*.

BACKGROUND OF THE INVENTION

Lyme disease is a multisystem, tick-borne disease produced by *B. burgdorferi*. "Lyme Disease," United States, 1991–1992, MMWR 42:345–348 (1993). It is characterized by recurrent systemic and local manifestations involving the skin, heart, nervous system and joints. Lyme disease has three clinical stages. Steere, A. C., "Lyme Disease," *N. Engl. J. Med.*, 321:586–596 (1989). Stage I lasts approximately four weeks, and includes skin rashes such as erythema chronicum and general influenza-like systemic symptoms. An asymptomatic period is followed by Stage II, characterized by musculoskeletal, nervous and cardiac system involvement. Arthritis is the major manifestation of Stage III. The clinical manifestations of Lyme disease are probably due to a mixture of infection by tissue-invasive *B. burgdorferi*, specific host immune responses to *B. burgdorferi* antigens, and autoimmune reactions triggered by *B. burgdorferi* antigens. Steere, A. C., "Lyme Disease," *N. Engl. J. Med.*, 321:586–596 (1989); Duffy, J. "Lyme Disease," *Infect. Dis. Clin. N. Am.*, 1:511–527 (1987); Marcus, L. C., et al., "Fatal Pancarditis In A Patient With Coexistent Lyme Disease and Babesiosis. Demonstration Of Spirochetes In The Myocardium," *Ann. Inter. Med.*, 103:374–376 (1986).

The role of infection by *B. burgdorferi* in the pathogenesis of Lyme disease is suggested by the presence of *B. burgdorferi* in tissues (Marcus, L. C., et al., "Fatal Pancarditis In A Patient With Coexistent Lyme Disease and Babesiosis. Demonstration Of Spirochetes In The Myocardium," *Ann. Inter. Med.*, 103:374–376 (1986); Syndman, D. R., et al., "*Borrelia Burgdorferi* In Joint Fluid In Chronic Lyme Arthritis," *Ann. Inter. Med.*, 104:798–800 (1986)), the strong anti-*B. burgdorferi* cellular and humoral response in Lyme disease patients (Szczepanski, A., et al., "Lyme Borreliosis: Host Responses to *Borrellia burgdorferi*," *Microbiol. Rev.*, 55:21–34–22 (1991); Rahn, D. W., "Lyme Disease: Clinical Manifestations, Diagnosis, and Treatment," *Sem. Arthritis Rheum.*, 20:201–218 (1991)), the effectiveness of antibiotic treatment in forestalling clinical manifestations of Stages I, II and III (Steere, A. C., et al., "Successful Parenteral Penicillin Therapy of Established Lyme Arthritis," *N. Engl. J. Med.*, 308:733–740 (1985); Steere, A. C., et al., "Treatment Of The Early Manifestations of Lyme Disease," *Ann. Inter. Med.*, 99:22–26 (1983)). Infection with *B. burgdorferi* is not the entire story in Lyme disease pathogenesis. However, processes associated with hypersensitivity and autoimmunity also appear to play an important role in at least some of the chronic manifestations of Lyme disease. Evidence for this includes treatment failure of antibiotics in half of patients with arthritis (Steere, A. C., et al., "Successful Parenteral Penicillin Therapy of Established Lyme Arthritis," *N. Engl. J. Med.*, 308:733–740 (1985); Steere, A. C., et al., "Treatment Of The Early Manifestations of Lyme Disease," *Ann. Inter. Med.*, 99:22–26 (1983)), the presence of anti-*B. burgdorferi* immune complexes in synovial fluid in the absence of demonstrable organisms (Steere, A. C., et al., "Chronic Lyme Arthritis: Clinical and Immunogenetic Differentiation Form Rheumatoid Arthritis," *Ann. Inter. Med.*, 90:896–901 (1979)), heavy infiltration of the synovia of affected joints with T lymphocytes (Yssel, H., et al., "*Borrelia Borgdorferi* Activates a T Helper Type 1-Like T Cell Subset In Lyme Arthritis," *J. Exp. Med.*, 174:593–601 (1991); Steere, A. C., et al., "Elevated Levels Of Collagenase And Prostaglandin E2 From Synovium Associated With Erosion Of Cartilage And Bone In A Patient With Chronic Lyme Arthritis," *Arthritis Rheum*, 23:591–599 (1983)), histological similarities of Lyme disease arthritis and rheumatoid arthritis (Yssel, H., et al., "*Borrelia Borgdorferi* Activates a T Helper Type 1-Like T Cell Subset In Lyme Arthritis," *J. Exp. Med.*, 174:593–601 (1991); Steere, A. C., et al., "Elevated Levels Of Collagenase And Prostaglandin E2 From Synovium Associated With Erosion Of Cartilage And Bone In A Patient With Chronic Lyme Arthritis," *Arthritis Rheum*, 23:591–599 (1983)), and cross-reactivity of *B. burgdorferi* antigens with human tissue (Fikrig, E., et al., "Serologic Response To The *Borrelia Burgdorferi* Flagellin Demonstrates An Epitope Common To A Neuroblastoma Cell Line," *Proc. Natl. Acad. Sci. USA*, 90:183–187 (1993)). *B. burgdorferi* can also directly stimulate production of cytokines such as interleukins-1, 2, and 6, interferons, and tumor necrosis factor from normal, uninfected lymphoid cells, synovial cells and rat glioma cells. Miller, L. C., et al., "Balance Of Synovial Fluid IL-1β and IL-1 Receptor Antagonist And Recovery From Lyme Arthritis," *Lancet*, 341:146–148 (1993); Habicht, G. S., et al., "Cytokines And The Pathogenesis Of Neuroborreliosis: *Borrelia Burgdorferi* Induces Glioma Cells To Secrete Interleukin-6," *J. Infect. Dis.*, 164:568–574 (1991). This could be important for Lyme disease pathogenesis since interleukin-1 can itself stimulate the production of collagenase and prostaglandin E2 by synovial cells and fibroblasts. Steere, A. C., et al., "Elevated Levels Of Collagenase And Prostaglandin E2 From Synovium Associated with Erosion Of Cartilage And Bone In A Patient With Chronic Lyme Arthritis," *Arthritis Rheum*, 23:591–599 (1983). The occurrence of hypersensitivity and autoimmunity in Lyme disease underscores the need to exclude *B. burgdorferi* antigens able to trigger these phenomena from any proposed Lyme disease vaccine.

*B. burgdorferi* are taxonomically and antigenically complex. *B. burgdorferi sensu lato* consists of at least three genospecies (I, II, III), defined on the basis of genomic and antigenic similarities, and includes other non-classifiable strains (see Table I, below). Branton, G., et al., "Delineation of *Borrelia Burgdorferi Sensu Stricto, Borrelia Garinii* Sp. Nov., And Group VS461 Associated With Lyme Borreliosis," *Int. J. Syst. Bacteriol*, 42:378–383 (1992); Canica, M. M., et al., "Monoclonal Antibodies For Identification Of *Borrelia Afzelii* Sp. Nov. Associated With Late Cutaneous Manifestations Of Lyme Borreliosis," *Scand. J. Infect. Dis.*, 25:441–448 (1993); Belfaiza, J., et al., "Genomic Fingerprinting of *Borrelia Burgdorferi Sensu Lato* By Pulse-Field Gel Electrophoresis," *J. Clin. Microbiol.*, 31:2873–2877 (1993). *B. burgdorferi sensu strictu* consists only of genospecies I. Branton, G., et al., "Delineation of *Borrelia Burgdorferi Sensu Stricto, Borrelia Garinii* Sp. Nov., And Group VS461 Associated With Lyme Borreliosis," *Int. J. Syst. Bacteriol*, 42:378–383 (1992); Canica, M. M., et al., "Monoclonal Antibodies For Identification Of *Borrelia Afzelii* Sp. Nov. Associated With Late Cutaneous Manifestations Of Lyme Borreliosis," *Scand. J.*

Infect. Dis., 25:441–448 (1993); Belfaiza, J., et al., "Genomic Fingerprinting of *Borrelia Burgdorferi Sensu Lato* By Pulse-Field Gel Electrophoresis," *J. Clin. Microbiol.*, 31:2873–2877 (1993). In addition to antigenic variability between strains ((Szczepanski, A., et al., "Lyme Borreliosis: Host Responses To *Borrelia Burgdorferi*," *Microbiol. Rev.*, 55:21–34–22 (1991); Barbour, A. G., "Biological And Social Determinants Of The Lyme Disease Problem," *Infect. Agents Dis.*, 1:50–61 (1992)), a given strain may show antigenic variations in different hosts, after exposure to host defenses in a single host, and/or after repeated laboratory passages (Barbour, A. G., et al., "Biology Of Borrelia Species," *Microbiol. Rev.*, 50:381–400 (1986)). The antigenic complexity of *B. burgdorferi* has in turn complicated development of vaccines and diagnostic assays for Lyme disease.

The surface of *B. burgdorferi*, the bacterial structure that interacts with the mammalian immune system, is composed of a layer of carbohydrates covering an outer sheath or cell membrane. Barbour, A. G., et al., "Biology Of Borrelia Species," *Microbiol. Rev.*, 50:381–400 (1986). This membrane is composed of a variety of proteins including OspA-E, a lipopolysaccharide, and a peptidoglycan. Barbour, A. G., et al., "Biology of Borrelia species," *Microbiol. Rev.*, 50:381–400 (1986); Bergstrom, S., et al., "Molecular Analysis Of Linear Plasmid-encoded Major Surface Proteins, OspA and OspB, Of The Lyme Disease Spirochete *Borrelia burgdorferi*," *Molec. Microbiol.*, 3:479–486 (1989); Fuchs, R., et al., "Molecular Analysis And Expression Of A *Borrelia burgdorferi* Gene Encoding A 22kDa Protein (pC) in *Escherichia coli*," *Molec. Microbiol.*, 6:503–509 (1992); Lam, T. T., et al., "Outer Surface Proteins E and F of *Borrelia burgdorferi*, The Agent Of Lyme Disease," *Infect. Immun.*, 62:290–298 (1994); Beck, G., et al., "Chemical And Biologic Characterization Of A Lipopolysaccharide From The Lyme Disease Spirochete (*Borrelia burgdorferi*)," *J. Infect. Dis.*, 152:108–117 (1985); Takayama, K., et al., "Absence of Lipopolysaccharide In The Lyme Disease Spirochete, *Borrelia burgdorferi*," *Infect. Immun.*, 55:2311–2313 (1987). The existence of the latter two structures in *B. burgdorferi* is still controversial. Beck, G., et al., "Chemical And Biologic Characterization Of A Lipopolysaccharide From The Lyme Disease Spirochete (*Borrelia burgdorferi*)," *J. Infect. Dis.*, 152:108–117 (1985); Takayama, K., et al., "Absence of Lipopolysaccharide In The Lyme Disease Spirochete, *Borrelia burgdorferi*," *Infect. Immun.*, 55:2311–2313 (1987). OspA and OspB lipoproteins are analogous to the VMP proteins of *B. hermsii*, and appear to undergo extensive variation among *B. burgdorferi* genotypes and isolates in vitro and in vivo. This variability can be detected by both gene and gene product analysis. Marconi, R. T., et al., "Variability Of osp Genes And Gene Products Among Species of Lyme Disease Spirochetes," *Infect. Immun.*, 61:2611–2617 (1993); Schoberg, R. J., et al., "Identification Of A Highly Cross-reactive Outer Surface Protein B Epitope Among Diverse Geographic Isolates of Borrelia Spp. Causing Lyme Disease," *Infect Immun.*, 32:489–500 (1994). It appears to be responsible for the ability of *B. burgdorferi* to become resistant to the bactericidal effects of anti-OspA/OspB antibodies. Sădžiene, A., et al., "Antibody-resistant Mutants of *Borrelia burgdorferi*: In Vitro Selection And Characterization," *J. Exp. Med.*, 176:799–809 (1992); Coleman, J. L., et al, "Selection Of An Escape Variant Of *Borrelia burgdorferi* By Use Of Bactericidal Monoclonal Antibodies To OspB," *Infect. Immun.*, 60:3098–3104 (1992). Antibodies against OspA prevent development of carditis in the scid mouse. Schaible, U. E., et al., "Monoclonal Antibodies Specific For The Outer Membrane Protein A (OspA) Of *Borrelia burgdorferi* Prevent Lyme Disease Borreliosis In Severe Combined Immunodeficiency (Scid) Mice," *Proc. Natl. Acad. Sci. USA*, 87:3768–3772 (1990). The immunogenicity of OspA appears to be influenced by its lipidic content (Erdile,, L. F., et al., "Role Of Attached Lipid In Immunogenicity Of *Borrelia burgdorferi* OspA," *Infect. Immun.*, 61:81–90 (1993)), and, as mentioned above, the protein has been used successfully as a vaccine in animals (Fikrig, E., et al., "Protection Of Mice Against The Lyme Disease Agent By Immunizing With Recombinant OspA," *Science*, 250:553–556 (1990)). The heterogeneity of these *B. burgdorferi* plasmid-encoded proteins is not unexpected. We have reported that *E. coli* plasmid genes appear to have an increased potential for variation as they usually have a higher replication rate than the bacterial chromosome and carry insertion sequences and transposons. Timmis, K., et al., "Instability Of Plasmid Sequences: Macro And Microevolution Of The Antibiotic Resistance Plasmids R6-5," *Mol. Gen. Genet.*, 167:11–19 (1978). All these properties increase the opportunities for emergence of mutations. Timmis, K., et al., "Instability Of Plasmid Sequences: Macro And Microevolution Of The Antibiotic Resistance Plasmids R6-5," *Mol. Gen. Genet.*, 167:11–19 (1978).

*B. burgdorferi* antigens cross-react with antigens of other pathogenic and human commensal spirochetes and with antigens of Gram-negative bacteria. Rasiah. C., et al., "Purification And Characterization Of A Tryptic Peptide Of *Borrelia burgdorferi* Flagellin, Which Reduces Cross-reactivity In Immunobolots And ELISA," *J. Gen. Microbiol.*, 138:147–154 (1992); Coleman, J. L., et al., "Characterization Of Antigenic Determinants Of *Borrelia burgdorferi* Shared By Other Bacteria," *J. Infect. Dis.*, 165:658–656 (1992). *B. burgdorferi* flagellin has 60–95% amino acid sequence similarity to flagellins from related bacteria (Rasiah. C., et al., "Purification And Characterization Of A Tryptic Peptide Of *Borrelia burgdorferi* Flagellin, Which Reduces Cross-reactivity In Immunobolots And ELISA," *J. Gen. Microbiol.*, 138:147–154 (1992); Coleman, J. L., et al., "Characterization Of Antigenic Determinants Of *Borrelia burgdorferi* Shared By Other Bacteria," *J. Infect. Dis.*, 165:658–656 (1992)), 50% to unrelated ones (Rasiah. C., et al., "Purification And Characterization Of A Tryptic Peptide of *Borrelia burgdorferi* Flagellin, Which Reduces Cross-reactivity In Immunobolots And ELISA," *J. Gen. Microbiol.*, 138:147–154 (1992); Coleman, J. L., et al., "Characterization Of Antigenic Determinants Of *Borrelia burgdorferi* Shared By Other Bacteria," *J. Infect. Dis.*, 165:658–656 (1992)), and cross-reacts with human tissue antigens as well (Rasiah. C., et al., "Purification And Characterization Of A Tryptic Peptide Of *Borrelia burgdorferi* Flagellin, Which Reduces Cross-reactivity In Immunobolots And ELISA," *J. Gen. Microbiol.*, 138:147–154 (1992); Magnarelli, L. A., et al., "Comparison Of Whole-cell Antibodies And An Antigenic Flagellar Epitope Of *Borrelia burgdorferi* In Serologic Tests For Diagnosis Of Lyme Borreliosis," *J. Clin. Microbiol.*, 30:3158–3162 (1992)). In general, there is a broad cross-reactivity of *B. burgdorferi* proteins with proteins of other bacterial species including Borrelia, Treponema, and gram-negative rods that are capable of inducing anamnestic responses. Coleman, J. L., et al., "Characterization Of Antigenic Determinants Of *Borrelia burgdorferi* Shared By Other Bacteria," *J. Infect. Dis.*, 165:658–656 (1992). Moreover, the surface of *B. burgdorferi* may be similar to the surface of *T. pallidum*, with major membrane proteins anchored by lipids to the outermost cytoplasmic membrane, thus potentially decreasing their immunogenicity. Cox, D. L., et al., "The Outer Membrane, Not A Coat Of Host Proteins, Limits Antigenicity Of Virulent *Treponema Pallidum*," *Infect. Immun.*, 60:1076–1083 (1992). Current studies utilizing immune responses to identify protective *B. burgdorferi* antigens as a basis for developing vaccines for Lyme disease have just begun, and their results have been problematic.

An approach to these problems is to examine immunogenic components of *B. burgdorferi* at the molecular level. Barbour, A. G., "Biological And Social Determinants Of The Lyme Disease Problem," *Infect. Agents Dis.*, 1:50–61 (1992); Bergstrom, S, et al., "Molecular Analysis Of Linear Plasmid-encoded Major Surface Proteins, OspA and OspB, Of The Lyme Disease Spirochete *Borrelia burgdorferi*," *Molec. Microbiol.*, 3:479–486 (1989). The genetic material of *B. burgdorferi* consists of double-stranded linear chromosomal DNA with a putative size of 990 kb, and linear and covalently closed DNA plasmids whose sizes range from 7.6 to 70.0 kb. Bergstrom, S., et al., "Molecular Analysis Of Linear Plasmid-encoded Major Surface Proteins, OspA and OspB, Of The Lyme Disease Spirochete *Borrelia burgdorferi*," *Molec. Microbiol.*, 3:479–486 (1989); Casjens, S., et al., "Linear Chromosomal Physical And Genetic Map Of *Borrelia burgdorferi*, The Lyme Disease Agent," *Molec. Microbiol.*, 8:967–980 (1993). A 49.0 kb linear plasmid encodes the expression of the immunogenic, polymorphic 31 kDa OspA and 34 kDa OspB outer membrane lipoproteins. These proteins share 53% identity in their amino acid sequences. Bergstrom, S., et al., "Molecular Analysis Of Linear Plasmid-encoded Major Surface Proteins, OspA and OspB, Of The Lyme Disease Spirochete *Borrelia burgdorferi*," *Molec. Microbiol.*, 3:479–486 (1989); Coleman, J. L., et al, "Selection Of An Escape Variant Of *Borrelia burgdorferi* By Use Of Bactericidal Monoclonal Antibodies To OspB," *Infect. Immun.*, 60:3098–3104 (1992). Their function in bacterial physiology and role in virulence is still unclear. Bergstrom, S., et al., "Molecular Analysis Of Linear Plasmid-encoded Major Surface Proteins, OspA and OspB, Of The Lyme Disease Spirochete *Borrelia burgdorferi*," *Molec. Microbiol.*, 3:479–486 (1989); Volkman, D. J., et al., "Characterization Of An Immunoreactive 93-kDa Core Protein Of *Borrelia burgdorferi* With A Human IgG Monoclonal Antibody," *J. Immunol.*, 146:3177–3182 (1991). Molecular genetic techniques have permitted cloning, expression, and sequencing of the plasmid-encoded OspA-F genes and the genes of other *B. burgdorferi* protein antigens (i.e. flagellin, p39, IpLA7 and heat-shock proteins). Bergstrom, S., et al., "Molecular Analysis Of Linear Plasmid-encoded Major Surface Proteins, OspA and OspB, Of The Lyme Disease Spirochete *Borrelia burgdorferi*," *Molec. Microbiol.*, 3:479–486 (1989); Fuchs, R., et al., "Molecular Analysis And Expression Of A *Borrelia burgdorferi* Gene Encoding A 22 kDa Protein (pC) in *Escherichia coli*," *Molec. Microbiol.*, 6:503–509 (1992); Lam, T. T., et al., "Outer Surface Proteins E and F of *Borrelia burgdorferi*, The Agent Of Lyme Disease," *Infect. Immun.*, 62:290–298 (1994). This has opened the way for chemical and structural characterization of their gene products and their purification in large amounts for use as vaccines and diagnostic reagents. Bergstrom, S., et al., "Molecular Analysis Of Linear Plasmid-encoded Major Surface Proteins, OspA and OspB, Of The Lyme Disease Spirochete *Borrelia burgdorferi*," *Molec. Microbiol.*, 3:479–486 (1989); Fuchs, R., et al., "Molecular Analysis And Expression Of A *Borrelia burgdorferi* Gene Encoding A 22 kDa Protein (pC) in *Escherichia coli*," *Molec. Microbiol.*, 6:503–509 (1992); Lam, T. T., et al., "Outer Surface Proteins E and F of *Borrelia burgdorferi*, The Agent Of Lyme Disease," *Infect. Immun.*, 62:290–298 (1994)); Volkman, D. J., et al., "Characterization Of An Immunoreactive 93-kDa Core Protein Of *Borrelia burgdorferi* With A Human IgG Monoclonal Antibody," *J. Immunol.*, 146:3177–3182 (1991); Wilske, B., et al., "Immunological And Molecular Polymorphisms Of OspC, An Immunodominant Major Outer Surface Protein Of *Borrelia burgdorferi*," *Infect. Immun.*, 61:2182–2191 (1993); Hansen, K., et al., "Immunochemical Characterization And Isolation Of The Gene For A *Borrelia burgdorferi* Immunodominant 60-Kilodalton Antigen Common To A Wide Range Of Bacteria," *Infect. Immun.*, 56:2047–2053 (1986). Little is known, however, about the role of OspA-F, flagella, the 60 kDa and 73 kDa proteins, or any *B. burgdorferi* antigens, for that matter, in infection of ticks or production of disease in mammals during the different stages of Lyme disease. Barbour, A. G., "Biological And Social Determinants Of The Lyme Disease Problem,"*Infect. Aqents Dis.*, 1:50–61 (1992).

The infected host develops immune responses to *B. burgdorferi* outer surface membrane antigens, periplasmic antigens such as flagella, and cytoplasmic antigens such as heat-shock proteins. Rasiah, C., et al., "Purification And Characterization Of A Tryptic Peptide Of *Borrelia burgdorferi* Flagellin, Which Reduces Cross-reactivity In Immunobolots And ELISA," *J. Gen. Microbiol.*, 138:147–154 (1992); Hansen, K., et al., "Immunochemical Characterization And Isolation Of The Gene For A *Borrelia burgdorferi* Immunodominant 60-Kilodalton Antigen Common To A Wide Range Of Bacteria," *Infect. Immun.*, 56:2047–2053 (1986). Such responses have been detected by ELISA, IFA, immunoblotting, and T cell mitogenesis. Krause, A., et al., "Cellular Immune Reactivity To Recombinant OspA And Flagellin From *Borrelia Burgdorferi* In Patients With Lyme Borreliosus," *J. Clin. Invest.*, 90:1077–1084 (1992); Fikrig, E., et al., "Serologic Diagnosis Of Lyme Disease Using Recombinant Outer Surface Proteins A And B And Flagellin," *J. Infect. Dis.*, 165:1127–1132 (1992). Some of the humoral response comprises protective antibodies that can inhibit *B. burgdorferi* growth and/or are bactericidal. Pavia, C. S., et al., "Antiborrelial Activity Of Serum From Rats Injected With The Lyme Disease Spirochete," *J. Infect. Dis.*, 163:656–659; Sadziene, A., et al., "In Vitro Inhibition of *Borrelia burgdorferi* Growth By Antibodies," *J. Infect. Dis.*, 167:165–172 (1993); Fikrig, E., et al., "Long-Term Protection Of Mice From Lyme Disease By Vaccination With OspA," *Infect. Immun.*, 60:773–777 (1992). However, there are wide individual variations in human serological response to *B. burgdorferi* (Barbour, A. G., "Biological And Social Determinants Of The Lyme Disease Problem," *Infect. Agents Dis.*, 1:50–61 (1992); Corpuz, M., et al., "Problems In The Use Of Serologic Tests For The Diagnosis Of Lyme Disease," *Ann. Inter. Med.*, 151:1837–1840 (1991)), and high titers of specific antibodies may be demonstrable only late in the evolution of disease (Barbour, A. G., "Biological And Social Determinants Of The Lyme Disease Problem," *Infect. Agents Dis.*, 1:50–61 (1992); Corpuz, M., et al., "Problems In The Use Of Serologic Tests For The Diagnosis Of Lyme Disease," *Ann. Inter. Med.*, 151:1837–1840 (1991)). Cross reactivity of *B. burgdorferi* antigens with host antigens may induce host tolerance and host autoimmunity. Fikrig, E., et al., "Serologic Response To The *Borrelia Burgdorferi* Flagellin Demonstrates An Epitope Common To A Neuroblastoma Cell Line," *Proc. Natl. Acad. Sci. USA*, 90:183–187 (1993). The small numbers of bacteria apparently found in tissues and fluids in Lyme disease may conspire against a robust humoral immune response. Duray, P. H., "Capturing Spirochetes From Humans," *Am. J. Clin. Pathol.*, 99:4–6 (1993); Dattwyler, R. J., et al., "Seronegative Lyme Disease. Dissociations of Specific T- and B-lymphocytes Responses to *B. burgdorferi*," *N. Engl. J. Med.*, 319:141–1446 (1988)), and the possible intracellular location of the bacteria in macrophages or other immunologically hidden sites may exacerbate this situation (Montgomery, R. R., et al., "The Fate Of *Borrelia burgdorferi*, The Agent For Lyme Disease, In Mouse Macrophages," *J. Immunol,* 150:909–915 (1993)). Furthermore, some patients show dissociation between humoral and cell-mediated immune responses, with a lack of serological response to infection in the presence of strong T cell reactivity to *B. burgdorferi* antigens (Lahesmas, R., et al., "Preferential Use Of T Cell Antigen Receptor V Region Gene Segment Vbeta5.1 By *Borrelia Burgdorferi* Antigen-reactive T Cell Clones Isolated From A Patient With Lyme Disease," *J. Immunol.,* 150:4125–4135 (1993)).

Host immune response to *B. burgdorferi* is influenced by genetic factors in the host as well as by the antigens expressed by the infecting *B. burgdorferi* strain. In human beings, immune response to *B. burgdorferi* and development of clinical manifestations of Lyme disease can depend on HLA haplotypes. Golde, W. T., et al., "The Major Histocompatibility Complex-restricted Response Of Recombinant Inbred Strains Of Mice To Natural Tick Transmission Of *Borrelia burgdorferi,*" *J. Exp. Med.,* 177:9–17 (1993). In mice, disease-susceptible (C3H) and disease-resistant (BALB/c) inbred strains have been found (De Souza, M. S., et al., "Long-Term Study Of Cell-Mediated Responses to *Borrelia burgdoferi* In The Laboratory Mouse," *Infect. Immun.,* 61:1884–1822 (1993)), and patterns of antibody response to *B. burgdorferi* antigens are MHC-restricted in mice infected by natural tick transmission of *B. burgdorferi* (Golde, W. T., et al., "The Major Histocompatibility Complex-restricted Response Of Recombinant Inbred Strains Of Mice To Natural Tick Transmission of *Borrelia burgdorferi,*" *J. Exp. Med.,* 177:9:17 (1993)).

Study and interpretation of the humoral and cellular immune responses to *B. burgdorferi* antigens in Lyme disease is complicated by the complex mixes of *B. burgdorferi* antigens used in these studies and the absence of antigenic standardization. Barbour, A. G., "Biological And Social Determinants Of The Lyme Disease Problem," *Infect. Agents Dis.,* 1:50–61 (1992). ELISA results may vary because of fluctuations in amounts of particular *B. burgdorferi* antigens bound to solid phases from the diverse antigenic mixtures of whole cell sonicates. Schwartz, B. S., et al., "Antibody Testing In Lyme Disease: A Comparison Of Results In Four Laboratories," *JAMA,* 262:3431–3434 (1989); Luger, S. W., et al., "Serologic Tests For Lyme Disease: Interlaboratory Variability," *Arch. Intern. Med.,* 150:761–763 (1990); Bakken. L. L., et al., "Performance of 45 Laboratories Participating In A Proficiency Testing Program For Lyme Disease Serology," *JAMA,* 268:891–895 (1992). In immunoblots, the apparent lack of reactivity of a serum with given *B. burgdorferi* antigens may be due to an inability to resolve antigens of similar molecular weight (Karlsson, M, et al., "Comparison Of Western Blot And Enzyme-linked Immunosorbent Assay For Diagnosis Of Lyme Borreliosis," *Eur. J. Clin. Microbiol. Infect. Dis.,* 8:871–877 (1989); Aron-Hott, L., et al., "Lipopolysaccharide-independent Radioimmunoprecipitation And Identification Of Structural And in vivo Induced Immunogenic Surface Proteins of *Salmonella typhi* In Typhoid," *Vaccine,* 11:10–17 (1993)), to denaturation of conformational epitopes produced by SDS-polyacrylamide gel electrophoresis (SDS-PAGE) (Karlsson, M., et al., "Comparison Of Western Blot And Enzyme-linked Immunosorbent Assay For Diagnosis Of Lyme Borreliosis," *Eur. J. Clin. Microbiol. Infect. Dis.,* 8:871–877 (1989); Aron-Hott, L., et al., "Lipopolysaccharide-independent Radioimmunoprecipitation And Identification Of Structural And in vivo Induced Immunogenic Surface Proteins of *Salmonella typhi* In Typhoid," *Vaccine,* 11:10–17 (1993)), or to low antigenic concentration in the sample (Karlsson, M., et al., "Comparison Of Western Blot And Enzyme-linked Immunosorbent Assay For Diagnosis Of Lyme Borreliosis," *Eur. J. Clin. Microbiol. Infect. Dis.,* 8:871–877 (1989); Aron-Hott, L., et al., "Lipopolysaccharide-independent Radioimmunoprecipitation And Identification Of Structural And in vivo Induced Immunogenic Surface Proteins of *Salmonella typhi* In Typhoid," *Vaccine,* 11:10–17 (1993)). Cross-contamination of one *B. burgdorferi* antigen with another in SDS-PAGE and non-specific binding of immunoglobulins to denatured *B. burgdorferi* proteins can also interfere with the interpretation of immunoblots. Karlsson, M, et al., "Comparison Of Western Blot And Enzyme-linked Immunosorbent Assay For Diagnosis Of Lyme Borreliosis," *Eur. J. Clin. Microbiol. Infect. Dis.,* 8:871–877 (1989); Aron-Hott, L., et al., "Lipopolysaccharide-independent Radioimmunoprecipitation And Identification Of Structural And in vivo Induced Immunogenic Surface Proteins of *Salmonella typhi* In Typhoid," *Vaccine,* 11:10–17 (1993).

Protection against *B. burgdorferi* infection and subsequent development of Lyme disease can be achieved by immunization with killed *B. burgdorferi* cells or with purified antigens of this bacteria. Fikrig, E., et al., "Protection Of Mice Against The Lyme Disease Agent By Immunizing With Recombinant OspA," *Science,* 250:553–556 (1990); Fikrig, E., et al., "Long-Term Protection Of Mice From Lyme Disease By Vaccination With OspA," *Infect. Immun.,* 60:773–777 (1992); Fikrig, et al., "OspA Vaccination Of Mice With Established *Borrelia burgdoferi* Infection Alters Disease But Not Infection," *Infect. Immun.,* 61:2553–2557 (1993). Adoptive transfer of T cells from chronically-infected C3H mice failed to prevent infection and disease development in recipient C3H mice. De Souza, M. S., et al., "Long-Term Study Of Cell-Mediated Responses to *Borrelia burgdoferi* In The Laboratory Mouse," *Infect. Immun.,* 61:1884–1822 (1993). These observations are consistent with induced protection being primarily mediated by antibodies against borrelial antigens, and not by T cell-mediated cellular immune responses. Fikrig, E., et al., "Protection Of Mice Against The Lyme Disease Agent By Immunizing With Recombinant OspA," *Science,* 250:553–556 (1990); Fikrig, E., et al., "Long-Term Protection Of Mice From Lyme Disease By Vaccination With OspA," *Infect. Immun.,* 60:773–777 (1992). Antisera against *B. burgdorferi* OspA/OspB proteins have been used to provide passive protection against *B. burgdorferi* infection in scid and C3H/HeJ mice; immunization of these mouse strains with rOspA/rOspB protein provides active protection. Schaible, U. E., et al., "Monoclonal Antibodies Specific For The Outer Membrane Protein A (OspA) Of *Borrelia burgdorferi* Prevent Lyme Disease Borreliosis In Severe Combined Immunodeficiency (Scid) Mice," *Proc. Natl. Acad. Sci. USA,* 87:3768–3772 (1990); Fikrig, E., et al., "Long-Term Protection Of Mice From Lyme Disease By Vaccination With OspA," *Infect. Immun.,* 60:773–777 (1992); Fikrig, et al., "OspA Vaccination Of Mice With Established *Borrelia burgdoferi* Infection Alters Disease But Not Infection," *Infect. Immun.,* 61:2553–2557 (1993). In scid mice, however, passive protection appears to be complete only for infection by *B. burgdorferi* expressing identical or very similar OspA. Schaible, U. E., "Immune Sera To Individual *Borrelia burgdoferi* Isolates Or Recombinant OspA Thereof Protect SCID Mice Against Infection with Homologous Strains But Only Partially Or Not At All Against Those Of Different OspA/OspB Genotype," *Vaccine,* 11:1049–1054 (1993). This is due to variation in the genes and gene products of the OspA/OspB operon among various *B. burgdorferi* genotypes and different isolates of the same genotype. Marconi, R. T., et al., "Variability Of osp Genes And Gene Products Among Species of Lyme Disease Spirochetes," *Infect. Immun.,* 61:2611–2617 (1993). Similarly, vaccination of C3H/HeJ mice with truncated rOspA fails to elicit protective immunity, while *B. burgdorferi* expressing truncated OspB are able to escape immune destruction in mice vaccinated with OspB. Bockenstedt, L. K., et al., "Inability Of Truncated Recombinant OspA Proteins To Elicit Protective Immunity To *Borrelia burgdoferi* In Mice," *J. Immunol.*, 151:900–906 (1993); Fikrig, E., et al., "Evasion Of Protective Immunity By *Borrelia burgdoferi* By Truncation Of Outer Surface Protein B.," *Proc. Nat. Acad. Sci. USA*, 90:4092–4096) (1993). *B. burgdorferi* variants lacking expression of OspA/OspB are still able to confer protection to immunized mice even against challenges with strains expressing OspA/OspB antigens. Norton Hughes, C. A., et al., "Protective Immunity Is Induced By A *Borrelia burgdoferi* Mutant That Lacks OspA and OspB," *Infect. Immun.*, 61:5151–5122 (1993). These experiments suggest that plasmid-encoded OspA/OspB are not the only *B. burgdorferi* antigens that can confer protection. Norton Hughes, C. A., et al., "Protective Immunity Is Induced By A *Borrelia burgdoferi* Mutant That Lacks OspA and OspB," *Immun.*, 61:5151–5122 (1993). Another property of plasmids that makes plasmid-encoded gene products less suitable for use in vaccines is the non-essential nature of plasmids to bacterial survival, because they are lost during cell division with relatively high frequency. Timmis, K., et al., "Instability Of Plasmid Sequences: Macro And Microevolution Of The Antibiotic Resistance Plasmids R6-5," *Mol. Gen. Genet.*, 167:11–19 (1978). For example, vaccination of animal and human populations with *B. burgdorferi* plasmid-encoded OspA/OspB could potentially select for the emergence and dissemination of strains expressing different OspA/OspB proteins or lacking the expression of these dispensable proteins altogether. Timmis, K., et al., "Instability Of Plasmid Sequenced: Macro And Microevolution Of The Antibiotic Resistance Plasmids R6-5," *Mol. Gen. Genet.*, 167:11–19 (1978); Schaible, U. E., "Immune Sera To Individual *Borrelia burgdoferi* Isolates Or Recombinant OspA Thereof Protect SCID Mice Against Infection with Homologus Strains But Only Partially Or Not At All Against Those Of Different OspA/OspB Genotype," *Vaccine*, 11:1049–1054 (1993); Bockenstedt, L. K., et al., "Inability Of Truncated Recombinant OspA Proteins To Elicit Protective Immunity To *Borrelia burgdoferi* In Mice," *J. Immunol.*, 151:900–906 (1993); Norton Hughes, C. A., et al., "Protective Immunity Is Induced By A *Borrelia burgdoferi* Mutant That Lacks OspA and OspB," *Infect. Immun.*, 61:5151–5122 (1993).

In view of the above-noted deficiencies in the art, the need remains for improved procedures to detect and treat Lyme disease. The present invention is directed to meeting this objective.

SUMMARY OF THE INVENTION

The present invention relates to an isolated membrane protein or polypeptide encoded by chromosomal DNA of *Borrelia burgdorferi*. The isolated protein or polypeptide of the present invention can be combined with a pharmaceutically-acceptable carrier to form a vaccine or used alone for administration to mammals, particularly humans, in preventing infection by *Borrelia burgdorferi*. Alternatively, the protein or polypeptide of the present invention can be used to raise an antibody or a binding portion thereof. The antibody or binding portions thereof may be used alone or combined with a pharmaceutically-acceptable carrier to treat mammals, particularly humans, already exposed to *Borrelia burgdorferi*, to induce a passive immunity to prevent disease occurrence.

The present invention also relates to an isolated DNA molecule encoding the membrane protein or polypeptide of the present invention. The molecule can be inserted as a heterologous (i.e. not naturally present) DNA in an expression vector forming a recombinant DNA expression system for producing the protein or polypeptide. Likewise, the heterologous DNA, usually inserted in the expression vector to form a recombinant DNA expression system, can be incorporated in a host cell to express the protein or polypeptide.

The protein or polypeptide of the present invention or the antibodies or binding portions thereof raised against them can be utilized in a method for detection of *Borrelia burgdorferi* or responses induced in infected hosts in a sample of tissue or body fluids. When the protein or polypeptide is utilized, it is provided as an antigen. Any reaction with the antigen or the antibody is detected using an assay system which indicates the presence of *Borrelia burgdorferi* or host immune response to it in the sample. Alternatively, *Borrelia burgdorferi* can be detected in such a sample by providing a nucleotide sequence of the gene encoding protein or polypeptide of the present invention as a probe in a nucleic acid hybridization assay or a gene amplification detection procedure (e.g., using a polymerase chain reaction procedure). Any reaction with the probe is detected so that the presence of *Borrelia burgdorferi* in the sample is indicated.

Isolation of the protein or polypeptide of the present invention constitutes a significant advance in the treatment and detection of *Borrelia burgdorferi*. Since it is a chromosomally-encoded gene product of *Borrelia burgdorferi*, it provides a more genetically stable immunogen for a Lyme disease vaccine than plasmid-encoded gene products. Moreover, such proteins or polypeptides lack cross-reactivity with host antigens and are able to stimulate immunity in all recipients. The absence of such cross-reactivity permits the protein or polypeptide of the present invention to function well in detection assays. The protein or polypeptide of the present invention can be produced at high levels using recombinant DNA technology.

BRIEF DESCRIPTION OF THE DRAWINGS

FIG. 1 shows the deduced amino acid sequence (SEQ. ID No. 1) and complete nucleotide sequence (SEQ. ID. No. 2) of the *Borrelia burgdorferi* BmpC proteins and bmpC gene, respectively. Potential promoters are indicated by a double underline. A ribosome binding site (positions 162–167) is underlined. The cysteine (amino acid residue 17) which may serve as a lipidation site is shown in bold. This sequence has been assigned GenBank Accession Number L34547.

DETAILED DESCRIPTION OF THE INVENTION

The present invention relates to an isolated membrane protein or polypeptide encoded by chromosomal DNA of

*Borrelia burgdorferi*. This isolated protein, BmpC, has a calculated isoelectric point of about 9.6. BmpC also has about a 35–45% homology to the BmpA and BmpB protein or polypeptide identified in W. J. Simpson, et al., "Nucleotide Sequence and Analysis of the Gene in *Borrelia burgdorferi* Encoding Immunogenic P39 Antigen," *FEMS Letters,* 119:381–88 (1994), which is hereby incorporated by reference. The BmpC protein or polypeptide has a calculated molecular weight of 39 to 40 kilodaltons. The BmpC protein or polypeptide of the present invention has one or more antigenic determinants conferring on the protein the ability to recognize antisera for mammals infected with *Borrelia burgdorferi*. The BmpC protein or polypeptide has an amino acid sequence corresponding to SEQ. ID. No. 1 as follows:

the proteins. If necessary, the protein fraction may be further purified by HPLC.

The DNA molecule of the present invention can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production

```
MFKRFIFITLSLLVFACFKSNKKSIKSDKVVVGVLAHGSFYDKGYNQSVHDGVVKLRDNF
GIKLITKSLRPYPIEGKRLLTVDEAMTEDAYEVQKNPLNLFWLIGYRFSDLSVKLSYERP
DIYYGIIDAFDYGDIQVPKNSLAIKFRNEEAAFLAGYIAAKMSRKEKIGFLTGPMSEHLK
DFKFGFKAGIFYANPKLRLVSKKAPSLFDKEKGKAMALFMYKEDKVGVIFPIAGITGLGV
YDAAKELGPKYYVIGLNQDQSYIAPQNVITSIIKDIGKVIYSISSEYINNRVFKGGIIID
RGLKEGVIEIVKDPDVLNNRLVDEVIDLENKIISGEIIVPDSEYAFDLFKSKL
```

In *Borrelia burgdorferi*, the protein or polypeptide of the present invention is believed to be present as a membrane lipoprotein.

Another aspect of the present invention relates to a DNA molecule encoding the protein or polypeptide of the present invention. As to the BmpC protein or polypeptide, the DNA molecule comprises a nucleotide sequence correspondending to SEQ. ID. No. 2 as follows:

of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

```
AAAAATTGATTTTTCCTACTACTGTGTTTTTATTAATGCTAGAAGTATTTTTTAAAAGG
GATTATTAAAATTTTATTTTATAAATAAAGAATACTGCTTGTTAGTAAAATAAAGTTAAT
ATTTTAATTTTTAAAAAATTTAGAATTTTAAAAAAAAATATAAGGAGAGGATTAATTTTG
TTTAAAAGATTTATTTTTATTACTTTATCTTTATTAGTATTTGCTTGTTTTAAATCTAAT
AAAAAGTCTATTAAATCTGACAAAGTTGTTGTAGGTGTTTTGGCTCATGGTAGCTTTTAT
GATAAAGGCTATAATCAAAGCGTTCATGATGGTGTTGTAAAACTTAGGGATAATTTTGGA
ATAAAGCTTATAACTAAATCTTTAAGACCTTATCCTATTGAGGGTAAAAGACTTCTTACT
GTTGATGAGGCAATGACTGAGGATGCTTATGAGGTTCAAAAAAATCCTTTAAATCTTTTT
TGGTTGATTGGATACCGATTTTCTGACTTGTCAGTTAAGCTTTCCTATGAACGTCCAGAT
ATTTATTATGGTATTATAGATGCTTTTGATTATGGTGATATTCAAGTTCCTAAGAATTCC
TTGGCTATTAAGTTTAGAAATGAAGAGGCTGCATTTTTAGCTGGGTATATTGCTGCTAAG
ATGAGCAGAAAAGAAAAGATTGGATTTTTAACAGGTCCTATGAGTGAGCATTTAAAAGAT
TTTAAGTTTGGTTTTAAGGCTGGAATTTTTTATGCCAATCCTAAATTAAGATTAGTTTCA
AAAAAAGCACCTTCTCTTTTTGATAAGGAGAAAGGCAAAGCAATGGCTCTATTCATGTAT
AAAGAAGATAAAGTAGGCGTTATTTTTCCAATAGCTGGTATAACTGGTCTTGGAGTTTAT
GACGCTGCTAAGGAGCTTGGACCTAAATATTATGTTATTGGTTTAAATCAAGATCAATCA
TATATTGCACCTCAAAATGTTATTACTTCAATAATTAAGGATATTGGTAAGGTTATTTAT
TCTATTTCATCAGAGTATATTAATAATAGAGTTTTTAAGGGTGGAATTATTATTGATCGG
GGGTTAAAGGAAGGAGTAATAGAAATTGTTAAGGATCCCGATGTTTTAAACAATAGGTTG
GTTGATGAAGTTATTGATCTAGAAAATAAAATAATAAGTGGAGAAATTATTGTTCCTGAT
AGTGAATATGCATTTGATTTATTTAAATCAAAGTTATAAACTACTTAAATATAGCTTTGT
TTGTAAAGGGGAAATAGTTTATGAATAAAATAT
```

In *Borrelia burgdorferi*, the BmpC DNA molecule is part of a gene located at about 400 kbp on a chromosomal map of *Borrelia burgdorferi*. It is immediately upstream of the genes encoding for the proteins BmpA and BmpB (i.e. bmpA and bmpB, respectively).

The protein or polypeptide of the present invention is preferably produced in purified form by conventional techniques. Typically, the protein of the present invention is secreted into the growth medium of recombinant *E. coli*. To isolate the protein, the *E. coli* host cell carrying a recombinant plasmid is propagated, homogenized, and the homogenate is centrifuged to remove bacterial debris. The supernantant is then subjected to sequential ammonium sulfate precipitation. The fraction containing the protein of the present invention is subjected to gel filtration in an appropriately sized dextran or polyacrylamide column to separate Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning:*

A Laboratory Manual, Cold Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promotors and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, Methods in Enzymology, 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in E. coli, its bacteriophages, or plasmids, promotors such as the T7 phage promoter, lac promotor, trp promotor, recA promotor, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other E. coli promotors produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in E. coli requires a Shine-Dalgarno (SD) sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the E. coli tryptophan E, D, C, B or A genes. Additionally, any SD-ATG combination produced by recombinant DNA or other techniques involving incorporation of synthetic nucleotides may be used.

Once the isolated DNA molecule of the present invention has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

In view of the present invention's discovery of the BmpC protein or polypeptide, a wide array of therapeutic and/or prophylatic agents and diagnostic procedures for, respectively, treating and detecting *Borrelia burgdorferi* can be developed.

For example, an effective amount of the protein or polypeptide of the present invention can be administered alone or in combination with a pharmaceutically-acceptable carrier to mammals, particularly humans, as a vaccine, for preventing infection by *Borrelia burgdorferi*. Alternatively, it is possible to administer to individuals exposed to *Borrelia burgdorferi* with an effective amount of an antibody or binding portion thereof against that protein or polypeptide as a passive immunization. Such antibodies or binding portions thereof are administered alone or in combination with a pharmaceutically-acceptable carrier to effect short term treatment of individuals who may have been recently exposed to *Borrelia burgdorferi.*

Antibodies suitable for use in inducing passive immunity can be monoclonal or polyclonal.

Monoclonal antibody production may be effected by techniques which are well-known in the art. Basically, the process involves first obtaining immune cells (lymphocytes) from the spleen of a mammal (e.g., mouse) which has been previously immunized with the antigen of interest (i.e. the protein or peptide of the present invention) either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. The virus is carried in appropriate solutions or adjuvants. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol (PEG) or other fusing agents (See Milstein and Kohler, *Eur. J. Immunol.* 6:511 (1976), which is hereby incorporated by reference). This immortal cell line, which is preferably murine, but may also be derived from cells of other mammalian species, including but not limited to rats and humans, is selected to be deficient in enzymes necessary for the utilization of certain nutrients, to be capable of rapid growth and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentabarbitol 150 mg/Kg IV. This and other procedures for raising polyclonal antibodies are disclosed in E. Harlow, et. al., editors, *Antibodies: A Laboratory Manual* (1988), which is hereby incorporated by reference.

The vaccines and passive immunization agents of this invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The solid unit dosage forms can be of the conventional type. The solid form can be a capsule, such as an ordinary gelatin type containing the protein or peptide of the present invention or the antibody or binding portion thereof of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The protein or polypeptide of the present invention or the antibody or binding portion thereof of this invention may also be administered in injectable dosages by solution or suspension of these materials in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the protein or polypeptide of the present invention or the antibody or binding portion thereof of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In yet another aspect of the present invention, the protein or polypeptide of the present invention can be used as antigens in diagnostic assays for the detection of immune cells or antibodies reactive against *Borrelia burgdorferi* in body fluids. Alternatively, the detection of that organism can be achieved with a diagnostic assay employing antibodies or binding portions thereof raised by such antigens. Such techniques permit detection of *Borrelia burgdorferi* in a sample of the following tissue or body fluids: blood, spinal fluid, sputum, pleural fluids, urine, bronchial alveolor lavage, lymph nodes, bone marrow, or other biopsied materials.

In one embodiment, the assay system has a sandwich or competitive format. Examples of suitable assays include an enzyme-linked immunosorbent assay, a radioimmunoassay, a gel diffusion pricipitin reaction assay, an immunodiffusion assay, an agglutination assay, a fluorescent immunoassay, a protein A immunoassay, or an immunoelectrophoresis assay.

In an alternative diagnostic embodiment of the present invention, the nucleotide sequence of the isolated DNA molecule of the present invention may be used as a probe in nucleic acid hybridization assays for the detection of *Borrelia burgdorferi* in various patient body fluids. The nucleotide sequence of the present invention may be used in any nucleic acid hybridization assay system known in the art, including, but not limited to, Southern blots (Southern, *J. Mol. Biol.*, 98:508 (1975); Northern blots (Thomas et al., *Proc. Nat'l Acad. Sci. USA*, 77:5201–05 (1980)); Colony blots (Grunstein et al., *Proc. Nat'l Acad. Sci. USA*, 72:3961–65 (1975), which are hereby incorporated by reference). Alternatively, the isolated DNA molecule of the present invention can be used in a gene amplication detection procedure (e.g., a polymerase chain reaction). See H. A. Erlich et. al., "Recent Advances in the Polymerase Chain Reaction", *Science* 252:1643–51 (1991), which is hereby incorporated by reference.

EXAMPLES

Example 1

Preparation and Screening of a *B. burgdorferi* λgt11 Expression Library

*B. burgdorferi* strain 297, infective for mice and rats, was grown to a concentration of $10^8$ cells/ml. Total DNA was purified from sonicated cells by phenol/chloroform extraction and ethanol precipitation, with special care being taken to minimize breakage of high molecular weight chromosomal DNA. Sambrook, J., et al., "Molecular Cloning. A Laboratory Manual," Cold Spring Harbor Laboratory Press, Cold Spring Harbor, N.Y. (1989) and Aguero, J., et al., "Cloning, Expression and Characterization of the 36 kDa *Salmonella typhi* in *Escherichia coli,*" *Microb. Pathogen.* 3:399–407 (1987), which are hereby incorporated by reference. This preparation was partially digested with EcoRI and ligated with an equimolar amount of EcoRI-digested λgt11 DNA. The ligation mix was packaged and transfected into *E. coli* Y1090 r. Sambrook, J., et al., "Molecular Cloning. A Laboratory Manual," Cold Spring Harbor Laboratory Press, Cold Spring Harbor, N.Y. (1989) and Hyunh, T. V., et al., "Constructing and Screening cDNA Libraries in λgt10 and λgt11. In: DNA Cloning" (Clover, D. M., Ed.) 1:49–78, IRL Press, Washington, D.C. (1986), which are hereby incorporated by reference. Initial screening of this library used a pool of polyclonal rabbit and human anti-*B. burgdorferi* antibodies to obtain as many immunogenic *B. burgdorferi* clones as possible before proceeding to narrower selective strategies. Hyunh, T. V., et al., "Constructing and Screening cDNA Libraries in λgt10 and λgt11. In: DNA Cloning" (Clover, D. M., Ed.) 1:49–78, IRL Press, Washington, D.C. (1986); Jendrisok, J., et al., "Cloning cDNA into λg10 and λgt11," Methods Enzymol. 152:359–371 (1987); and Mierendorf, R. C., et al., "Gene Isolation by Screening λgt11 Libraries," Methods Enzymol. 152:458–469 (1987), which are hereby incorporated by reference. Prior to pooling, human and rabbit sera were immunoabsorbed with rabbit and human IgG-Sepharose columns, respectively. Pooled sera were then repeatedly absorbed with *E. coli* Y1090 r cells, cell membranes, cytoplasmic proteins and ribosomes. Fernandez-Beros, et al., "Immune Response to the Iron-Deprivation-Induced Proteins of *Salmonella typhi* in Typhoid Fever," Infect. Immun. 57:1271–1275 (1989); Aron-Hott, et al., "Lipopolysaccharide-Independent Radio Immunoprecipitation and Identification of Structural and in vivo Induced Immunogenic Surface Proteins of *Salmonella typhi* in Typhoid," Vaccine 11:10–17 (1993); and Aron, L., "*Salmonella typhi* 0:9,12 Polysaccharide-Protein Conjugates: Characterization and Immunoreactivity with Pooled and Individual Normal Human Sera, Sera from Patients with Paratyphoid A and B and Typhoid Fever, and Animal Sera," J. Clin. Microbiol. 31:975–978 (1993), which are hereby incorporated by reference. Clones selected by this broad strategy were rescreened with individual acute and chronic Lyme disease patient and rabbit sera that were extensively absorbed using techniques similar to those used for the pooled sera until their non-specific reactivity was reduced to background levels which were acceptable for immunoscreening.

Example 2

Cloning Methods, DNA Sequence Analysis, and Southern Blotting

Extraction of chromosomal and plasmid DNA from *B. Burgdorferi* and *E. coli*, restriction enzyme analysis, elution of DNA fragments, ligation, transformation and selection of recombinant clones were performed as described in Aguero, J., et al., "Cloning, Expression and Characterization of the 36 kDa *Salmonella typhi* in *Escherichia coli*," Microb. Pathogen. 3:399–407 (1987) and Fernandez-Beros, et al., "Immune Response to the Iron-Deprivation-Induced Proteins of *Salmonella typhi* in Typhoid Fever," Infect. Immun. 57:1271–1275 (1989), which are hereby incorporated by reference. Primer synthesis and DNA sequencing were performed, as described in Schwartz, J. J., et al., "RNA Gene Organization in the Lyme Disease Spirochete, *Borrelia burgdorferi*," J. Bacteriol. 174:3757–3765 (1992), which is hereby incorporated by reference. The double-stranded dideoxy method with modified T7 DNA polymerase (SEQUENASE, U.S. Biochemicals, Cleveland, Ohio) was used for manual DNA sequencing and an Applied Biosystems (Foster City, Calif.) Model 373 DNA sequencer was used for automated sequencing. Computer analysis of the DNA sequences was performed with the PC/Gene software package (Intelligenetics, Inc., Palo Alto, Calif.), and the DNA and deduced amino acid sequences compared to entries in the GenBank and Swiss-Prot databases using the facilities of the BLAST E-mail server at the National Center for Biotechnology Information. Altschul, S. F., et al., "Basic Local Alignment Search Tool," J. Mol. Biol. 215:403–410 (1990), which is hereby incorporated by reference. Southern blot hybridization was performed essentially as described in Schwartz, J. J., et al., "RNA Gene Organization in the Lyme Disease Spirochete, *Borrelia burgdorferi*," J. Bacteriol. 174:3757–3765 (1992), which is hereby incorporated by reference, except that the probes were labelled with digoxigenin, and blots were developed using the Genius kit according to the manufacturer's instructions (Boehringer-Mannheim, Indianapolis, Ind.).

The nucleotide sequence (SEQ. ID No. 2) of *B. burgdorferi* bmpc presented in FIG. 1 was deposited in the GenBank/LANL database with the Accession Number L34547.

Example 3

Immunoscreening of *B. burgdorferi* λgt11 Genomic Library

Eleven thousand plaques from the unamplified, IPTG-induced *B. burgdorferi* λgt11 library were screened with an optimized dilution of absorbed human-rabbit serum pool. This number of plaques is over two and half times more than needed to obtain representation of each chromosomal and plasmid gene of *B. burgdorferi* at least once. Hyunh, T. V., et al., "Constructing and Screening cDNA Libraries in λgt10 and λgt11. In: DNA Cloning" (Clover, D. M., Ed.) 1:49–78. IRL Press, Washington, D.C. (1986); Jendrisok, J., et al., "Cloning cDNA into λg10 and λgt11," Methods Enzymol. 152:359–371 (1987); Mierendorf, R. C., et al., "Gene Isolation by Screening λgt11 Libraries," Methods Enzymol. 152:458–469 (1987), which is hereby incorporated by reference. One hundred fifty-four bacteriophages reacted positively with the pooled sera. Those bacteriophage clones giving the strongest signals in the initial immunoscreening were rescreened with absorbed individual normal human and Lyme disease patient sera. Several of these clones reacted with every one of the 16 individual sera from patients with early and late Lyme disease and did not react with any normal human serum. One recombinant clone was unreactive with mouse anti-OspA and anti-OspB monoclonal antibodies and with rabbit anti-OspC sera. It was designated LA006 and chosen for further studies.

Example 4

Sequence Analysis of Clone LA006 and Cloning of bmpC

Agarose gel electrophoresis and DNA restriction enzyme analysis indicated that clone LA006 contained an 6.4 kb insert of *B. burgdorferi* DNA. This insert was recloned in pUC19 and designated pLA007; a 5.2 kb BamH1 fragment from the insert was subcloned into pUC19 to yield pLA008. DNA sequencing of these clones with a pUC19 forward primer revealed an open reading frame (ORF) whose deduced amino acid sequence showed significant homology to *Treponema pallidum* TmpC, a putative membrane lipoprotein. Schouls, L. M., et al., "Characterization of the 35-Kilodalton *Treponema pallidum* subsp. pallidum Recombinant Lipoprotein TmpC and Antibody Response to Lipidated and Nonlipidated *T. pallidum* Antigens," Infect. Immun. 59:3536–3546 (1991), which is hereby incorporated by reference. This ORF was designated BmpC. No other sequences with significant homology were identified in the databases using the BLASTP algorithm on the NCBI mail server. Altschul, S. F., et al., "Basic Local Alignment Search Tool," J. Mol. Biol. 215:403–410 (1990), which is hereby incorporated by reference.

Two additional overlapping *B. burgdorferi* clones that included part of the BmpC ORF were used to obtain the complete nucleotide sequence of its gene, bmpC. Total *B. burgdorferi* DNA was digested with either BglII or PstI and the fragments were separated by agarose gel electrophoresis. Those which hybridized with a bmpC-specific probe were eluted and cloned into pUC19 to yield one clone containing a 3.8 kb Bgl/II fragment and a second clone containing a 2.4 kb PstI fragment.

Example 5

DNA Sequence Analysis of *Borrelia burgdorferi* bmpC

The complete DNA sequence of *B. burgdorferi* bmpC, including 177 nucleotides upstream and 57 nucleotides downstream of the open reading frame, is presented in FIG. 1. The ORF, beginning at residue 178, is 1059 nucleotides long and would encode a protein of 353 amino acids. It is preceded by a ribosome binding site (AAGGAG; FIG. 1) with 6 bp complementarity to the 3' end of *B. burgdorferi* 16S RNA (Gazumyan, A., "Sequence Analysis of the Ribosomal RNA Operon of the Lyme Disease Spirochete, *Borrelia burgdorferi,*" *Gene,* 146:57–65 (1994), which is hereby incorporated by reference) and is initiated with a TTG codon. The use of UUG as an initiation codon has been previously described in other bacteria. McCarthy, J. E. G., et al., "Translational Control of Prokaryotic Gene Expression," *Trends in Genet.* 6:78–85 (1990), which is hereby incorporated by reference. This may be the result of the inefficient use of a UUG initiation codon by the *E. coli* host. Ringquist, S., et al., "Translation Initiation in *Escherichia coli*: Sequences Within the Ribosome Binding site," *Mol. Microbiol.* 6:1219–1229 (1992), which is hereby incorporated by reference. The ORF is preceded by two regions which could function as $\sigma^{70}$-type promoters. The first of these consists of −35 and −10 consensus sequences at nucleotides 6–11 and 32–38, respectively. The second potential promoter is located at nucleotides 99–104 (−35 site) and 123–128 (−10 site) (FIG. 1).

The putative bmpC gene product has a calculated $M_r$ of 39,830 and an estimated pI of 9.57. Amino acid residues 13–17 are LVFAC, a consensus signal peptidase II site (Wu, H. C., et al., "Biogenesis of Lipoproteins in Bacteria," *Curr. Top. Microbiol. Immunol.* 125:127–157 (1986), which is hereby incorporated by reference) suggesting that BmpC is a lipoprotein. Additional sequencing and restriction analysis indicates that bmpC is located immediately upstream of the recently described bmpA and bmpB (Simpson, W. J., et al., "Nucleotide Sequence and Analysis of the Gene in *Borrelia burgdorferi* Encoding Immunogenic P39 Antigen," *FEMS Microbiol. Letters* 119:381–388 (1994), which is hereby incorporated by reference) at approximately 400 Kbp on the linear *B. burgdorferi* chromosome map. Casjens, S., et al., "Linear Chromosomal Physical and Genetic Map of *Borrelia burgdorferi*, the Lyme Disease Agent," *Mol. Microbiol.* 8:967–980 (1993), which is hereby incorporated by reference. bmpC is separated from the downstream bmpA by 40 nucleotides; the latter ORF begins with the ATG at nucleotide 1281 in FIG. 1. Simpson, W. J., et al., "Nucleotide Sequence and Analysis of the Gene in *Borrelia burgdorferi* Encoding Immunogenic P39 Antigen," *FEMS Microbiol. Letters* 119:381–388 (1994), which is hereby incorporated by reference. The location of these genes in tandem in a unique region of the *B. burgdorferi* chromosome could imply that they comprise a single transcriptional unit. As noted, above, two putative promoter sequences occur upstream of bmpC. Simpson, W. J., et al., "Nucleotide Sequence and Analysis of the Gene in *Borrelia burgdorferi* Encoding Immunogenic P39 antigen," *FEMS Microbiol. Letters* 119:381–388 (1994), which is hereby incorporated by reference, suggested the existence of a potential promoter 5' to bmpA. The −35 and −10 regions which they reported correspond to nucleotides 1214–1219 and 1235–1240, respectively, of the sequence shown in FIG. 1. This would place the putative promoter within the bmpC coding region. In addition, no recognizable promoter-like sequences were found upstream of bmpB. Simpson, W. J., et al., "Nucleotide Sequence and Analysis of the Gene in *Borrelia burgdorferi* Encoding Immunogenic P39 Antigen," *FEMS Microbiol. Letters* 119:381–388 (1994), which is hereby incorporated by reference. These observations strengthen the notion of a single transcriptional unit for these three genes which is initiated from a promoter 5' to bmpC.

Example 6

Figure 2A:
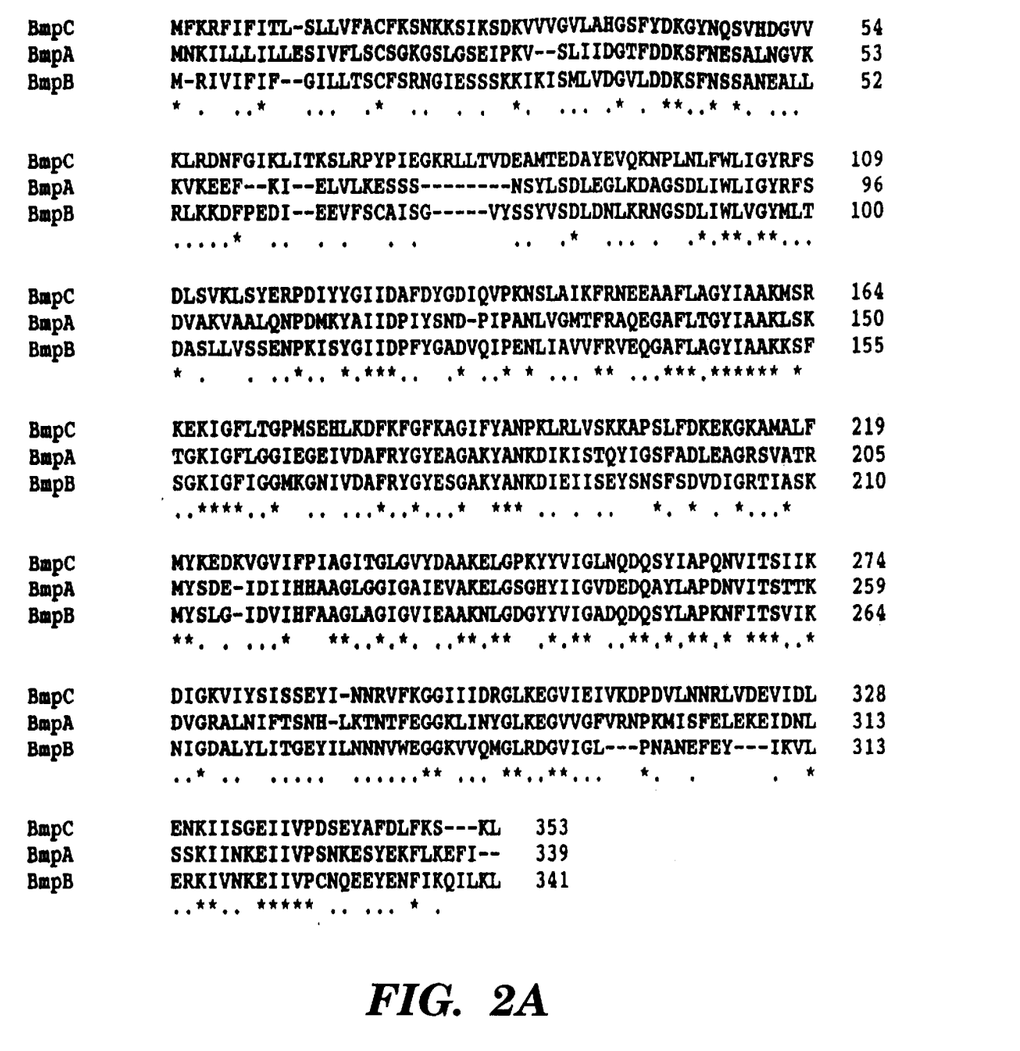
FIG. 2A shows the alignment of the deduced amino acid sequences of BmpC (SEQ. ID. No. 1), BmpA (SEQ. ID. No. 3), and BmpB (SEQ. ID. No. 4) of *B. burgdorferi*. Identical amino acid residues which occur at the same position in all three sequences are indicated by an asterisk (*). The presence of similar residues at those positions is denoted by a dot (.). For this analysis, the following residues are considered similar: A,S and T;D and E;N and Q;R and K;I, L,M and V;F, Y and W.

Comparison of BmpC with Sequences of Other *B. burgdorferi* and *T. pallidum* Proteins The deduced amino acid sequence of BmpC shares 39% and 40% identity with those of BmpA and BmpB, respectively. Simpson, W. J., et al., "Nucleotide Sequence and Analysis of the Gene in *Borrelia burgdorferi* Encoding Immunogenic P39 Antigen," *FEMS Microbiol. Letters* 119:381–388 (1994). The three sequences show 26% sequence identity (i.e., identical amino acid residues are found at 93 positions) (FIG. 2A). It is interesting to note that despite the significant degree of sequence identity, the estimated isoelectric point of BmpC is quite different from those for BmpA and BmpB (9.57 vs. 4.99 and 4.86, respectively). The tandem arrangement of these three coding regions, and the high degree of sequence similarity between them, suggests that they may have arisen from a single gene by duplication.

Figure 2B:
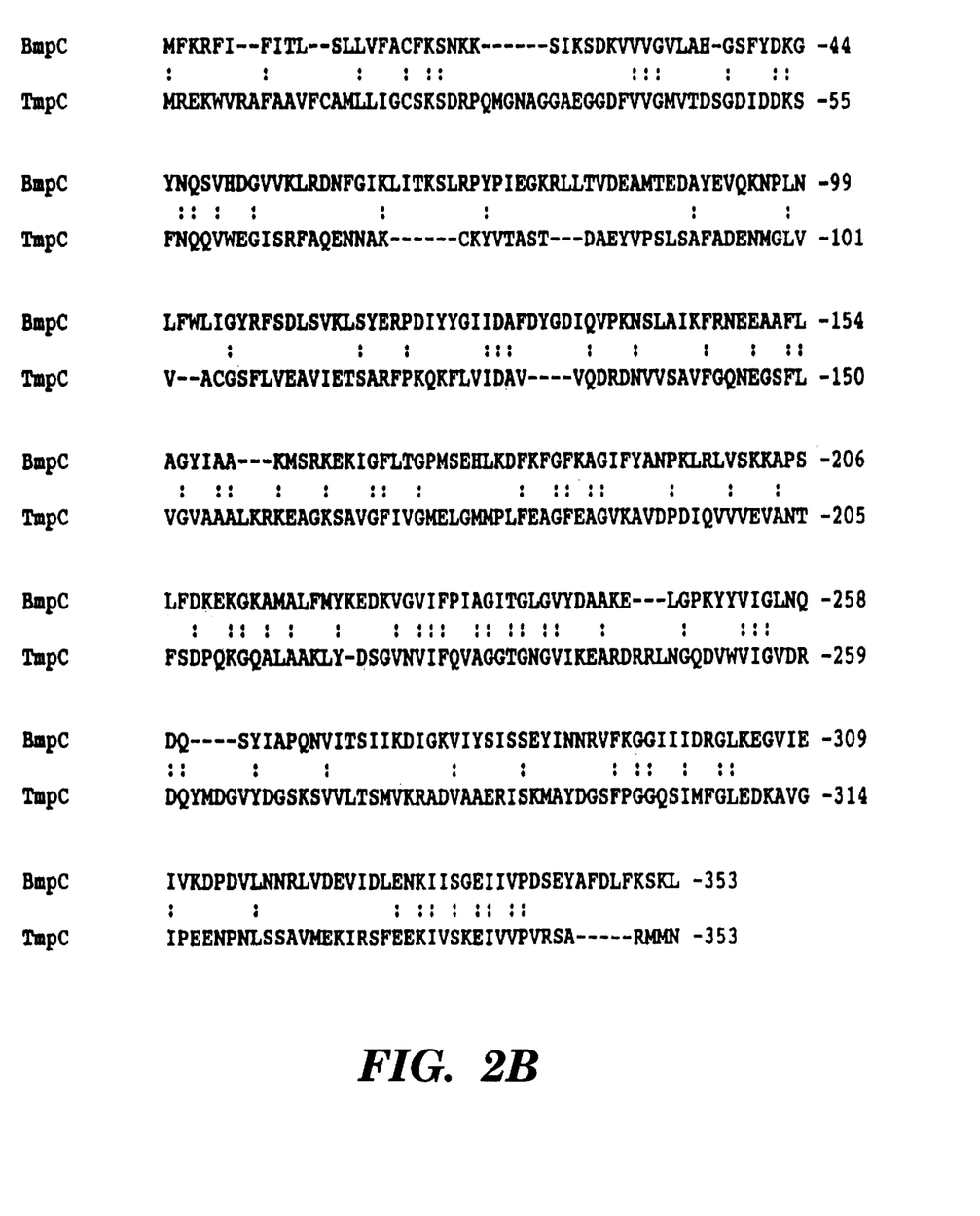
FIG. 2B shows the amino acid alignment of Bmpc (SEQ. ID. No. 1) with TmpC of *T. pallidum* (SEQ. ID. No. 5). Identical amino acid residues of BmpC at a specific position are indicated by a colon (:).

The sequence identity of BmpC with *T. pallidum* TmpC is 26% (FIG. 2B). This is similar to that reported previously for BmpA and BmpB with TmpC (27% and 32%, respectively). Simpson, W. J., et. al., "Nucleotide Sequence and Analysis of the Gene in *Borrelia burgdorferi* Encoding Immunogenic P39 Antigen," *FEMS Microbiol. Letters,* 119:381–88 (1994), which is hereby incorporated by reference. All these proteins have consensus signal peptidase II sites, suggesting that they are lipoproteins and are probably located in either the cytoplasmic or outer membrane of *Borrelia burgdorferi.*

Example 7

Presence of bmpC in Representative Isolates of *B. burgdorferi sensu lato*

Figure 3:
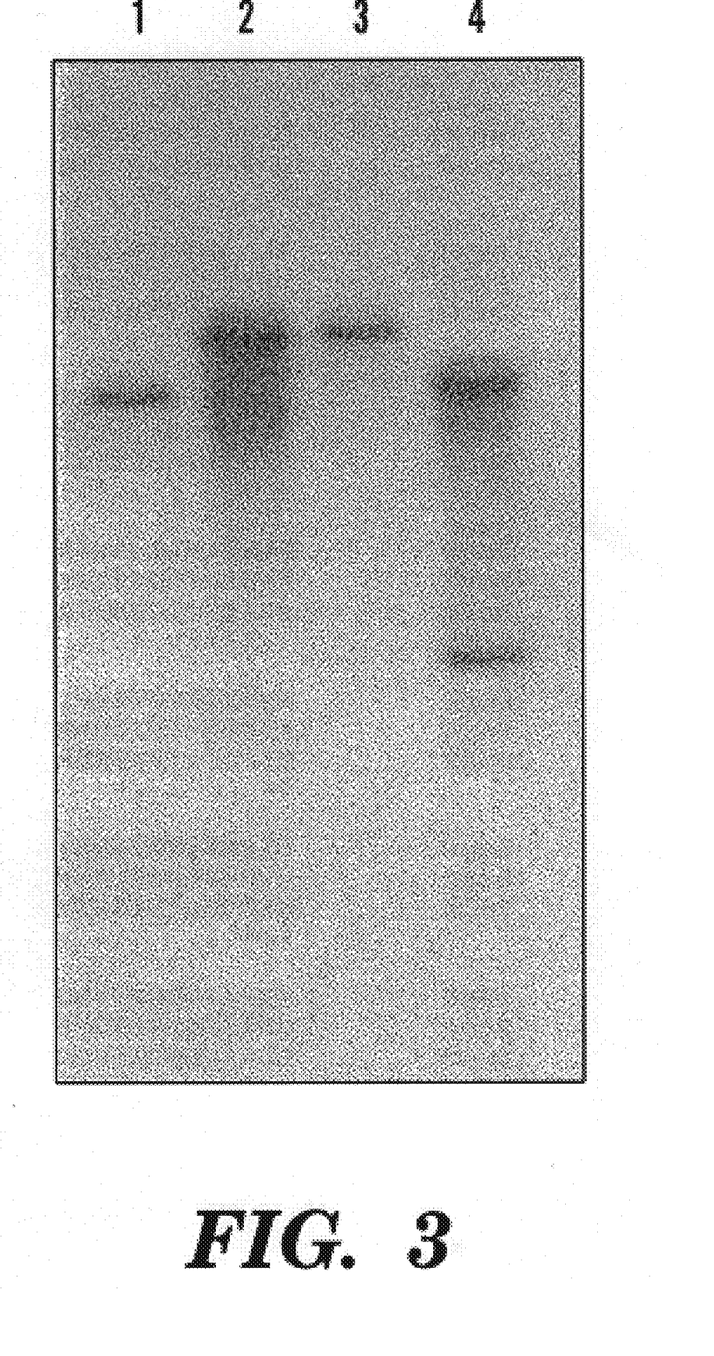
FIG. 3 shows the presence of the bmpC gene encoding the BmpC protein or polypeptide in all *B. burgdorferi sensu lato* genospecies. Genomic DNA from the indicated species was digested with HincII, separated on 0.8% agarose gel, blotted to a nylon membrane, and probed with bmpC-specific fragment. Lane 1: strain 297 (*B. burgdorferi sensu stricto*); Lane 2: strain 20047 (*B. garinii*); Lane 3: strain IP90 (*B. garinii*); Lane 4: strain IP3 (*B. afzelii*).

Southern blot hybridization experiments were performed in order to determine if bmpC was present in all *B. burgdorferi* strains. Chromosomal DNA from representative *B. burgdorferi sensu stricto* (strain 297), *B. garinii* (strains 20047 and IP90) and *B. afzelii* (strain IP3) were digested with HincII and the resultant blot was developed with a bmpC probe (FIG. 3). bmpC is present in all species. Interestingly, there are variations in the molecular mass of the hybridizing bands. *B. afzelii* strain IP3 also has an additional, smaller band, suggesting genetic variation of the DNA sequences in this region of the *B. burgdorferi* chromosome.

The Bmp proteins described here and by Simpson, W. J., et al., "Nucleotide Sequence and Analysis of the Gene in *Borrelia burgdorferi* Encoding Immunogenic P39 Antigen," *FEMS Microbiol. Letters* 119:381–388 (1994), which is hereby incorporated by reference, are the first examples of *B. burgdorferi* membrane proteins which are chromosomally encoded. As such they may be useful reagents in the diagnosis and prevention of Lyme disease since their sequences should be less subject to variation than those of the well-characterized Osp proteins which are all plasmid encoded. Howe, T. R., et al, "Organization of Genes Encoding Two Outer Membrane Proteins of the Lyme Disease Agent *Borrelia burgdorferi* Within a Single Transcriptional Unit," *Infect. Immun.* 54:207–212 (1986); Marconi, R. T., et al., "Transcriptional Analysis and Mapping of the ospC Gene in Lyme Disease Spirochetes," *J. Bacteriol.* 175:926–932 (1993), which is hereby incorporated by reference. The similarity in the amino acid sequences of the Bmp membrane proteins and their location in what appears to be a single transcriptional unit in the chromosome of *B. burgdorferi* would suggest that they may be part of a single operon whose gene products serve related functions.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated DNA molecule encoding a protein or polypeptide having an amino acid sequence of SEQ. ID. No. 1 or comprising a nucleotide sequence of SEQ. ID. No. 2.

2. An isolated DNA molecule according to claim 1, wherein said protein or polypeptide is encoded by a gene located at about 400 kbp on a chromosomal map of *Borrelia burgdorferi*.

3. A recombinant DNA expression system comprising an expression vector into which is inserted a heterologous DNA molecule according to claim 1.

4. A recombinant DNA expression system according to claim 2, wherein the heterologous DNA molecule has the nucleotide sequence of SEQ. ID. No. 2.

5. A recombinant DNA expression system according to claim 3, wherein the heterologous DNA molecule is inserted into said vector in sense orientation and correct reading frame.

6. A host cell incorporating a heterologous DNA molecule according to claim 1.

7. A host cell according to claim 6, wherein the heterologous DNA molecule has the nucleotide sequence of SEQ. ID. No. 2.

8. A host cell according to claim 6, wherein the heterologous DNA molecule is inserted in a recombinant DNA expression system comprising an expression vector.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 353 amino acids
      (B) TYPE: amino acid
      (C) STRANDEDNESS: single
      (D) TOPOLOGY: linear    (ii) MOLECULE TYPE: protein    (xi) SEQUENCE DESCRIPTION: SEQ ID NO: 1:

```
Met Phe Lys Arg Phe Ile Phe Ile Thr Leu Ser Leu Leu Val Phe Ala
1               5                   10                  15

Cys Phe Lys Ser Asn Lys Lys Ser Ile Lys Ser Asp Lys Val Val Val
            20                  25                  30

Gly Val Leu Ala His Gly Ser Phe Tyr Asp Lys Gly Tyr Asn Gln Ser
        35                  40                  45

Val His Asp Gly Val Val Lys Leu Arg Asp Asn Phe Gly Ile Lys Leu
    50                  55                  60

Ile Thr Lys Ser Leu Arg Pro Tyr Pro Ile Glu Gly Lys Arg Leu Leu
65                  70                  75                  80

Thr Val Asp Glu Ala Met Thr Glu Asp Ala Tyr Glu Val Gln Lys Asn
                85                  90                  95

Pro Leu Asn Leu Phe Trp Leu Ile Gly Tyr Arg Phe Ser Asp Leu Ser
                100                 105                 110

Val Lys Leu Ser Tyr Glu Arg Pro Asp Ile Tyr Tyr Gly Ile Ile Asp
            115                 120                 125

Ala Phe Asp Tyr Gly Asp Ile Gln Val Pro Lys Asn Ser Leu Ala Ile
        130                 135                 140

Lys Phe Arg Asn Glu Glu Ala Ala Phe Leu Ala Gly Tyr Ile Ala Ala
145                 150                 155                 160

Lys Met Ser Arg Lys Glu Lys Ile Gly Phe Leu Thr Gly Pro Met Ser
                165                 170                 175

Glu His Leu Lys Asp Phe Lys Phe Gly Phe Lys Ala Gly Ile Phe Tyr
            180                 185                 190

Ala Asn Pro Lys Leu Arg Leu Val Ser Lys Lys Ala Pro Ser Leu Phe
        195                 200                 205

Asp Lys Glu Lys Gly Lys Ala Met Ala Leu Phe Met Tyr Lys Glu Asp
    210                 215                 220

Lys Val Gly Val Ile Phe Pro Ile Ala Gly Ile Thr Gly Leu Gly Val
225                 230                 235                 240

Tyr Asp Ala Ala Lys Glu Leu Gly Pro Lys Tyr Tyr Val Ile Gly Leu
                245                 250                 255

Asn Gln Asp Gln Ser Tyr Ile Ala Pro Gln Asn Val Ile Thr Ser Ile
            260                 265                 270

Ile Lys Asp Ile Gly Lys Val Ile Tyr Ser Ile Ser Ser Glu Tyr Ile
        275                 280                 285

Asn Asn Arg Val Phe Lys Gly Gly Ile Ile Ile Asp Arg Gly Leu Lys
    290                 295                 300

Glu Gly Val Ile Glu Ile Val Lys Asp Pro Asp Val Leu Asn Asn Arg
305                 310                 315                 320
```

```
Leu Val Asp Glu Val Ile Asp Leu Glu Asn Lys Ile Ile Ser Gly Glu
            325                 330                 335

Ile Ile Val Pro Asp Ser Glu Tyr Ala Phe Asp Leu Phe Lys Ser Lys
            340                 345                 350

Leu (2) INFORMATION FOR SEQ ID NO: 2:

(i) SEQUENCE CHARACTERISTICS:
        (A) LENGTH: 1293 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

AAAAATTGAT TTTTCCTACT ACTGTGTTTT TATTAATGCT AGAAGTATTT TTTTAAAAGG      60

GATTATTAAA ATTTTATTTT ATAAATAAAG AATACTGCTT GTTAGTAAAA TAAAGTTAAT     120

ATTTTAATTT TTAAAAAATT TAGAATTTTA AAAAAAAATA TAAGGAGAGG ATTAATTTTG     180

TTTAAAAGAT TTATTTTTAT TACTTTATCT TTATTAGTAT TTGCTTGTTT TAAATCTAAT     240

AAAAAGTCTA TTAAATCTGA CAAAGTTGTT GTAGGTGTTT TGGCTCATGG TAGCTTTTAT     300

GATAAAGGCT ATAATCAAAG CGTTCATGAT GGTGTTGTAA AACTTAGGGA TAATTTTGGA     360

ATAAAGCTTA TAACTAAATC TTTAAGACCT TATCCTATTG AGGGTAAAAG ACTTCTTACT     420

GTTGATGAGG CAATGACTGA GGATGCTTAT GAGGTTCAAA AAAATCCTTT AAATCTTTTT     480

TGGTTGATTG GATACCGATT TTCTGACTTG TCAGTTAAGC TTTCCTATGA ACGTCCAGAT     540

ATTTATTATG GTATTATAGA TGCTTTTGAT TATGGTGATA TTCAAGTTCC TAAGAATTCC     600

TTGGCTATTA AGTTTAGAAA TGAAGAGGCT GCATTTTTAG CTGGGTATAT TGCTGCTAAG     660

ATGAGCAGAA AAGAAAAGAT TGGATTTTTA ACAGGTCCTA TGAGTGAGCA TTTAAAAGAT     720

TTTAAGTTTG GTTTTAAGGC TGGAATTTTT TATGCCAATC CTAAATTAAG ATTAGTTTCA     780

AAAAAAGCAC CTTCTCTTTT TGATAAGGAG AAAGGCAAAG CAATGGCTCT ATTCATGTAT     840

AAAGAAGATA AGTAGGCGT TATTTTTCCA ATAGCTGGTA TAACTGGTCT TGGAGTTTAT     900

GACGCTGCTA AGGAGCTTGG ACCTAAATAT TATGTTATTG GTTTAAATCA AGATCAATCA     960

TATATTGCAC CTCAAAATGT TATTACTTCA ATAATTAAGG ATATTGGTAA GGTTATTTAT    1020

TCTATTTCAT CAGAGTATAT TAATAATAGA GTTTTTAAGG GTGGAATTAT TATTGATCGG    1080

GGGTTAAAGG AAGGAGTAAT AGAAATTGTT AAGGATCCCG ATGTTTTAAA CAATAGGTTG    1140

GTTGATGAAG TTATTGATCT AGAAAATAAA ATAATAAGTG GAGAAATTAT TGTTCCTGAT    1200

AGTGAATATG CATTTGATTT ATTTAAATCA AAGTTATAAA CTACTTAAAT ATAGCTTTGT    1260

TTGTAAAGGG GAAATAGTTT ATGAATAAAA TAT                                 1293
```